US008318446B2

(12) United States Patent
Khoshnan et al.

(10) Patent No.: US 8,318,446 B2
(45) Date of Patent: Nov. 27, 2012

(54) DNA-DAMAGE-INDUCED PROTEOLYSIS

(75) Inventors: Ali Khoshnan, South Pasadena, CA (US); Paul H Patterson, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 384 days.

(21) Appl. No.: 12/631,608

(22) Filed: Dec. 4, 2009

(65) Prior Publication Data
US 2010/0143945 A1 Jun. 10, 2010

Related U.S. Application Data

(60) Provisional application No. 61/201,016, filed on Dec. 5, 2008.

(51) Int. Cl.
*G01N 33/53* (2006.01)
(52) U.S. Cl. .................................................. 435/7.2
(58) Field of Classification Search .................. None
See application file for complete search history.

(56) References Cited

U.S. PATENT DOCUMENTS

| 6,649,654 | B1 | 11/2003 | Karin et al. |
| 2003/0232888 | A1 | 12/2003 | Karin et al. |

FOREIGN PATENT DOCUMENTS
WO    WO 02/29408    4/2002

OTHER PUBLICATIONS

International Search Report and Written Opinion, dated Sep. 8, 2010, for PCT/US/2009/066874.
Anne et al., 2007, Phosphorylation of huntingtin by cyclin-dependent kinase 5 is induced by DNA damage and regulates wild type and mutant huntingtin toxicity in neurons. J Neurosci 27: 7318-7328.
Bae et al., 2005, p53 mediates cellular dysfunction and behavioral abnormalities in Huntington's disease. Neuron 47: 29-41.
Baxter et al., 2006, IKKbeta/2 induces TWEAK and apoptosis in mammary epithelial cells. Development 133: 3485-3494.
Björkqvist et al., 2008, A novel pathogenic pathway of immune activation detectable before clinical onset in Huntington's disease. J Exp Med 205: 1869-1877.
Bogdanov et al, 2001, Increased oxidative damage to DNA in a transgenic mouse model of Huntington's disease. J Neurochem 79: 1246-1249.
Burke et al., 2003, BMS-345541 is a highly selective inhibitor of IκB kinase that binds at an allosteric site of the enzyme and blocks NF-κB-dependent transcription in mice. J. Biol. Chem., 278(3)1450-1456.
Chien et al. 1991, The two-hybrid system: a method to identify and clone genes for proteins that interact with a protein of interest. Proc. Natl. Acad. Sci. USA, 88: 9578-9582.
Cho et al., 2008, Role of microglial IKK{beta} in kainic acid-induced hippocampal neuronal cell death. Brain 131: 3019-3033.

Cittelly et al., 2007, Phosphorylation of Bcl-xL after spinal cord injury. J Neurosci Res 85: 1894-1911.
De Luca et al., 2008, A role for oxidized DNA precursors in Huntington's disease-like striatal neurodegeneration. PLoS Genet 4(11): e1000266.
Dragatsis et al., 2000, Inactivation of Hdh in the brain and testis results in progressive neurodegeneration and sterility in mice. Nat Genet 26: 300-306.
Du et al., 2005, Characterization of vinblastine-induced Bcl-xL and Bcl-2 phosphorylation: evidence for a novel protein kinase and a coordinated phosphorylation/dephosphorylation cycle associated with apoptosis induction. Oncogene 24(1): 107-117.
Enokido et al., 2008, Age-dependent change of HMGB1 and DNA double-strand break accumulation in mouse brain. Biochem Biophys Res Commun 376(1): 128-133.
Fan et al., 2000, Vinblastine-induced phosphorylation of Bcl-2 and Bcl-xL is mediated by JNK and occurs in parallel with inactivation of the Raf-1/MEK/ERK cascade, J. Biol. Chem. 275: 29980-29985.
Feng et al, 2006, p53 tumor suppressor protein regulates the levels of huntingtin gene expression. Oncogene 2: 1-7.
Gafni et al., 2004, Inhibition of calpain cleavage of huntingtin reduces toxicity: accumulation of calpain/caspase fragments in the nucleus. J Biol Chem 279: 20211-20220.
Gauthier et al., 2004, Huntingtin controls neurotrophic support and survival of neurons by enhancing BDNF vesicular transport along microtubules. Cell 118: 127-138.
Ghosh et al., 2007, Selective inhibition of NF-kappaB activation prevents dopaminergic neuronal loss in a mouse model of Parkinson's disease. Proc Natl Acad Sci USA 104(47): 18754-18759.
Gines et al., 2003, Enhanced Akt signaling is an early pro-survival response that reflects N-methyl-D-aspartate receptor activation in Huntington's disease knock-in striatal cells. J Biol Chem 278: 50514-50522.
Graham et al., 2006, Cleavage at the caspase-6 site is required for neuronal dysfunction and degeneration due to mutant huntingtin. Cell 125: 1179-1191.
Hacker et al., 2006, Regulation and function of IKK and IKK-related kinases. Sci. STKE (357): re13.
Herrmann et al., 2005, IKK mediates ischemia-induced neuronal death. Nat Med 11: 1322-1329.
Houghten et al., 1991, Generation and use of synthetic peptide combinatorial libraries for basic research and drug discovery. Nature 354: 84-86.
Huang et al., 2007, Phosphorylation of CBP by IKKalpha promotes cell growth by switiching the binding preference of CBP from p53 to NF-kappaB. Mol Cell 26: 75-87.
Illuzzi et al., 2009, DNA breakage and induction of DNA damage response proteins precede the appearance of visible mutant huntingtin aggregates. J. Neurosci. Res., 87: 733-747.
Jonas, 2006, BCL-xL regulates synaptic plasticity. Mol Interv 6: 208-222.
Kapahi et al., 2000, Inhibition of NF-kB Activation by arsenite through reaction with a critical cysteine in the activation loop of Iκb kinase, J. Biol. Chem. 275(46):36062-36066.

(Continued)

*Primary Examiner* — Michael Pak
(74) *Attorney, Agent, or Firm* — Knobbe, Martens, Olson & Bear LLP

(57) ABSTRACT

The present application provides methods for identifying compounds for inhibiting DNA damage-induced Htt proteolysis, and methods and compositions for protecting cells from DNA damage-induced cleavage of Htt.

24 Claims, 12 Drawing Sheets

OTHER PUBLICATIONS

Kempson et al., 2009, Novel tricyclic inhibitors of IkappaB kinase. J. Med. Chem., 52: 1994-2005.
Khoshnan et al, 2004, Activation of the IkappaB kinase complex and nuclear factor-kappaB contributes to mutant huntingtin neurotoxicity. J Neurosci 24: 7999-8008.
Khoshnan et al., 2009, IKKα and IKKβ regulation of DNA damage-induced cleavage of Huntingtin. PlosOne 4(6):e5768.
Kim et al., 2001, Caspase 3-cleaved N-terminal fragments of wild type and mutant huntingtin are present in normal and Huntington's disease brains, associate with membranes, and undergo calpain-dependent Cleavage. Proc Natl Acad Sci U S A 98: 12784-12789.
Kruman et al., 2004, Cell cycle activation linked to neuronal cell death initiated by DNA damage. Neuron 41: 549-556.
Kuo et al., 2008, Gamma-H2AX—a novel biomarker for DNA double-strand breaks. In Vivo 22: 305-309.
Lam et al., 1991, A new type of synthetic peptide library for identifying ligand-binding activity. Nature 354: 82-84.
Leavitt et al., 2006, Wild-type huntingtin protects neurons from excitotoxicity. J Neurochem 96: 1121-1129.
Lee et al., 2006, Memantine reduces striatal cell death with decreasing calpain level in 3-nitropropionic model of Huntington's disease. Brain Res 1118; 199-207.
Li et al., 1995, A huntingtin-associated protein enriched in brain with implications for pathology. Nature 378: 398-402.
Li et al., 2005, Enhanced NF-kappaB activation and cellular function in macrophages lacking IkappaB kinase 1 (IKK1). Proc Natl Acad Sci U S A 102: 12425-12430.
Lin et al., 1994, Sequence of the murine Huntington disease gene: evidence for conservation, alternate splicing and polymorphism in a triplet (CCG) repeat. Hum. Mol. Genet. 3(1): 85-92.
Lois et al., 2002, Germline transmission and tissue-specific expression of transgenes delivered by lentiviral vectors. Science 295: 868-872.
Lotharius et al., 2002, Effect of mutant alpha-synuclein on dopamine homeostasis in a new human mesence-phalic cell line. J Biol Chem 277: 38884-38894.
Lubin et al., 2007, The IkappaB kinase regulates chromatin structure during reconsolidation of conditioned fear memories. Neuron 55: 942-957.
Mattson et al., 2006, Roles for NF-kappaB in nerve cell survival, plasticity, and disease. Cell Death Differ 13: 852-860.
Ojo-Amaize et al., 2001, Hypoestoxide, a novel anti-inflammatory natural diterpene, inhibits the activity of IκB kinase. Cell Immunol., 209:149-157.
Platt et al., 1994, Independent regulation of adipose tissue-specificity and obesity response of the adipsin promoter in transgenic mice. J. Biol. Chem., 269: 28558-28562.
Politis et al., 2008, Hypothalamic involvement in Huntington's disease: an in vivo PET study. Brain 131: 2860-2869.
Qi et al., 2007, Proteome analysis of soluble nuclear proteins reveals that HMGB1/2 suppress genotoxic stress in polyglutamine diseases. Nat Cell Biol 9(4): 402-414.
Ratovitski et al., 2007, N-terminal proteolysis of full-length mutant huntingtin in an inducible PC12 cell model of Huntington's disease. Cell Cycle 6: 2970-2981.
Schmitt et al., 2007, Nuclear colocalization and interaction between bcl-xL and cdkl (cdc2) during G2/M cell-cycle checkpoint. Oncogene 26:5851-5865.
Songyang et al., 1993, SH2 domains recognize specific phosphopeptide sequences. Cell 72: 767-778.
Steffan et al., 2001, Histone deacetylase inhibitors arrest polyglutamine-dependent neurodegeneration in *Drosophila*. Nature 413: 739-743.
Tai et al., 2007, Microglial activation in presymptomatic Huntington's disease gene carriers. Brain 130: 1759-1766.
The Huntington's Disease Collaborative Research Group, 1993, A novel gene containing a trinucleotide repeat that is expanded and unstable on Huntington's disease chromosomes. Cell 72: 971-983.
Tobin et al., 2000, Huntington's disease: the challenge for cell biologists. Trends Cell Biol. 10: 531-536.
Valerio et al., 2006, NF-kappaB pathway: a target for preventing beta-amyloid (Abeta)-induced neuronal damage and Abeta42 production. Eur J Neurosci 23: 1711-1720.
Van Loo et al., 2006, Inhibition of transcription factor NF-kappaB in the central nervous system ameliorates autoimmune encephalomyelitis in mice. Nat Immunol 7: 954-961.
West et al., 2001, Calcium regulation of neuronal gene expression. Proc Natl Acad Sci U S A 98: 11024-11031.
Wexler et al., 2004, Venezuelan kindreds reveal that genetic and environmental factors modulate Huntington's disease age of onset. Proc Natl Acad Sci U S A 101: 3498-3503.
Wu et al., 2006, Molecular linkage between the kinase ATM and NF-kappaB signaling in response to genotoxic stimuli. Science 311: 1141-1146.
Yin et al., 1998, The anti-inflammatory agents aspirin and salicylate inhibit the activity of IκB kinase-beta. Nature 396: 77-80.
Zhang et al., 2006, Huntingtin inhibits caspase-3 activation. EMBO J 25: 5896-5906.
Zoghbi et al., 2000, Glutamine repeats and neurodegeneration. Annu. Rev. Neurosci. 23: 217-247.
Zuccato et al., 2001, Loss of huntingtin-mediated BDNF gene transcription in Huntington's disease. Science 293: 493-498.

DNA-DAMAGE-INDUCED PROTEOLYSIS

CROSS-REFERENCE TO RELATED APPLICATIONS

The present application claims priority under 35 U.S.C. §119(e) to U.S. Provisional Application No. 61/201,016, filed on Dec. 5, 2008, which is herein expressly incorporated by reference in its entirety.

STATEMENT REGARDING FEDERALLY SPONSORED R & D

This invention was made with government support under grant NINDS 5RO1NS55298 awarded by the National Institute of Neurological Disorders and Stroke. The government has certain rights in the invention.

BACKGROUND OF THE INVENTION

1. Field of the Invention

The present application relates generally to huntingtin (Htt) proteolysis, methods for identifying compounds for protecting a cell from DNA damage-induced Htt proteolysis, methods and compositions for protecting cells from DNA damages, and methods and compositions for treating neurological disorders.

2. Description of the Related Art of Various Embodiments

The huntingtin gene is the subject of U.S. Pat. No. 5,693,757, incorporated herein by reference. Expanded CAG repeats (40 and above), which form an abnormal polyglutamine (polyQ) stretch in the huntingtin (Htt) protein, result in a gain of toxic function and induce death in subpopulations of neurons in the striatum and cortex (Zoghbi et al. Annu. Rev. Neurosci. 23:217-247 (2000); Tobin et al. Trends Cell Biol. 10:531-536 (2000)).

Generation of N-terminal fragments of mutant Htt is thought to initiate neurotoxicity, culminating in HD (Gafni et al. J. Biol. Chem. 279: 20211-20220 (2004); Graham et al. Cell 125:1179-1191 (2006); Ratovitski et al. Cell Cycle, 6:2970-2981 (2007). Wild type Htt is also cleaved and inactivated by proteases, and its deletion in the central nervous system (CNS) promotes neurodegeneration and is deleterious for development. However, the signaling pathways that regulate Htt proteolysis are poorly understood.

SUMMARY OF SOME EMBODIMENTS

In some aspects, the present application provides methods for identifying a compound for protecting a cell from Htt proteolysis, including DNA damage induced Htt proteolysis. In some embodiments, the method for identifying a compound for protecting a cell from DNA damage-induced Htt proteolysis comprises: providing one or more compounds to be tested; identifying a compound that is an IKKβ inhibitor; and testing the compound identified as the IKKβ inhibitor for its ability to reduce the cleavage of Htt. The Htt can be wild type Htt or mutant Htt. In some embodiments, the cell is a neuron. In some embodiments, the compound is selected from a small molecule, a nucleic acid, a peptide, and an antibody. In some embodiments, identifying the IKKβ inhibitor comprises testing a compound for its ability to inhibit the ability of IKKβ to phosphorylate Bcl-xL. In other embodiments, identifying the IKKβ inhibitor comprises testing a compound for its ability to inhibit activation of one or more caspases.

In some embodiments, the method for identifying a compound for protecting a cell from DNA damage-induced Htt proteolysis comprises: providing one or more compounds to be tested; identifying which compound is selected from an IKKα activator, a Bcl-xL inducer, or some combination thereof; and testing the compound identified as an IKKα activator, a Bcl-xL inducer, or some combination thereof for its ability to reduce the cleavage of Htt. The Htt can be wild type Htt or mutant Htt. In some embodiments, the cell is a neuron. In some embodiments, the compound is selected from a small molecule, a nucleic acid, a peptide, and an antibody. In some embodiments, the ability of the compound to reduce the cleavage of Htt is tested by monitoring a cell's survival or through monitoring the cleaved Htt product. In some embodiments, identifying the IKKα activator comprises testing a compound for its ability to inhibit the phosphorylation of Bcl-xL. In some embodiments, identifying the IKKα activators comprises testing a compound for its ability to inhibit activation of one or more caspases. In some embodiments, identifying the Bcl-xL inducer comprises testing a compound for its ability to inhibit the phosphorylation of Bcl-xL.

In some aspects, the present application relates to a method for protecting at least one cell from DNA damage. In some embodiments, the method comprises: inhibiting DNA damage-induced Htt proteolysis in at least one cell by contacting at least one cell with at least one compound selected from an IKKβ inhibitor, an IKKα activator, and a Bcl-xL inducer. An Htt proteolysis inhibitor can be a small molecule, a nucleic acid, a peptide, or an antibody. In some embodiments, at least one compound is an IKKβ inhibitor. Examples of the IKKβ inhibitor include, but are not limited to, herbimycin, sodium salicylate, retinoid-related compounds, cyclopentenone prostaglandins, anti-IKKβ small hairpin RNAs (shRNAs), NF-κB essential modulator (NEMO) binding peptides, IKKα, BMS-345541 (4(2'-aminoethyl)amino-1,8-dimethylimidazo(1,2-a)quinoxaline), tricyclic based inhibitors of IKK (for example, oxazole-based IKK inhibitors, thiazole-based IKK inhibitors and imidazole-based IKK inhibitors), and some combination thereof. In other embodiments, the at least one compound is an IKKα activator. Examples of IKKα activators include, but are not limited to, insulin-like growth factors (IGF) (for example, IGF-1 and IGF-2), netrin, and some combination thereof. In still other embodiments, the at least one compound is a Bcl-xL inducer. Examples of Bcl-xL inducers include, but are not limited to, IKKα; green tea polyphenols (GTP); epigallocatechin gallate (EGCG); Bcl-xL; insulin-like growth factors (IGF), such as IGF-1 and IGF-2; brain-derived neurotrophic factor (BDNF); cystamine, memantine, and some combination thereof.

In some aspects, the present application relates to a kit for screening IKKα activator. In some embodiments, the kit comprises a control IKKα activator and a means for monitoring DNA damage-induced Htt proteolysis. In some aspects, the kit comprises a DNA damaging means, device, and/or chemical and a means for detecting Htt proteolysis. In some aspects, the present application relates to a method of identifying a compound for reducing Htt proteolysis, the method comprising the steps of inducing DNA damage in a cell comprising Htt protein and/or a Htt gene; administering a candidate compound; observing if the candidate compound reduces Htt proteolysis in the cell compared to the level of Htt proteolysis in the cell without the candidate compound. In some embodiments, the level of Htt proteolysis is directly observed. In some embodiments, the level of Htt proteolysis is indirectly observed (such as through cell death or survival).

In some aspects, the present application relates to a method for treating an individual, preferably a mammal and more preferably a human having, suspected of having and/or at risk of developing HD by administering a therapeutically effective amount of an Htt proteolysis inhibitor to the individual. In some embodiments, a composition containing one or more Htt proteolysis inhibitors are delivered intracranially, for example, by injection directly into brain tissue or by injection into the cerebrospinal fluid. In other embodiments, for example where an Htt proteolysis inhibitor is able to cross the blood brain barrier, the composition containing the Htt proteolysis inhibitor is administered peripherally. In some aspects, the present application provides for the use of a Htt proteolysis inhibitor for the preparation of a medicament for treating a DNA damage induced neurodegeneration disorder, such as Huntington's Disease.

BRIEF DESCRIPTION OF THE DRAWINGS

FIG. 1A is a picture showing differentiation of MESC2.10 neurons. Neuroblasts were transduced with an EGFP lentivirus. After differentiation for 9 days, cells were fixed and examined by a confocal microscope. TOTO-3 was used to stain the nuclei.

FIG. 1B is a western blot showing the expression of synapse markers in MESC2.10 neurons. Extracts from differentiated neurons (DPD, days post differentiation) were examined by Western blotting for expression of β-catenin and PSD-95. Bottom panel shows Western blot analysis of lysates from neurons maintained for different time points in culture stained for caspase-3 activation.

FIG. 1C shows that γ-H2aX accumulates in the nuclei of etoposide treated MESC2.10 neuron. Differentiated neurons treated with etoposide for 4 hours were fixed and stained with a rabbit anti-γ-H2aX (green). Anti-Tuj-1 was used to label the cytoplasm (red).

FIG. 1D is a western blot showing accumulation of γ-H2aX in the nuclear fraction of etoposide treated neurons over time examined by Western blotting with anti-γ-H2aX antibody. Lamin B-1 was used as loading control.

FIG. 2A shows etoposide activates IKKβ. IKK complexes were immunoprecipitated with anti-IKKγ antibody coupled to protein G agarose beads and assayed for kinase activity using GST-IκBα and 32P-γ-ATP. Products were examined by SDS-PAGE followed by autoradiography. The top panel shows kinase activity (KA) and the lower panel shows a western blot for IKKβ of similar immunoprecipitated complexes.

FIG. 2B shows that IKKα is constitutively active in MESC2.10 neurons. Lysates were first treated with a combination of anti-IKKβ and IKKγ antibodies coupled to agarose beads to deplete IKKγ/IKKβ/IKKα complex. IKKα complexes were then immunoprecipitated with anti-IKKα antibody conjugated to protein G agarose beads and assayed for kinase activity as described in part A. The top panel shows IKKα activity and the bottom panel shows the western blot for IKKα. Fold changes of IKK activity were quantified by measuring the band intensity using Image J, and compared to non-treated neurons.

FIG. 3A is a western blot showing that etoposide promotes Htt proteolysis and the promotion is inhibited by elevated IKKα expression. EGFP and IKKα-transduced neurons were treated with 10 μM of etoposide for the indicated times. Extracts were examined for Htt by Western blotting. The top panel shows staining with anti-Htt (mAb 2166) antibody. The asterisk indicates full-length endogenous Htt and the arrow shows the cleaved Htt products. The second panel shows staining for tubulin. Fold changes for full-length Htt levels were obtained by measuring the band intensity in each lane, normalized to tubulin and compared to non-treated control.

FIG. 3B shows that p53 accumulates in the nucleus of etoposide treated neurons. Nuclear extracts from MESC2.10 neurons were examined for the presence p53 by western blotting. Lanes 1-4 are nuclear extracts from MESC2.10 neurons with EGFP and lanes 5-8 are from neurons that were transduced with IKKα lentiviruses (FIG. 3C). Staining with anti-lamin B1 was used to ensure equal loading (bottom panel).

FIG. 3C is a western blot showing IKKα levels in the control and IKKα-expressing neurons. MESC2.10 neuroblasts were transduced with an IKKα recombinant lentivirus and differentiated as described below. EGFP lentivirus was used as a control. Top panel shows the western blot for IKKα and bottom panel is staining of the same blot for tubulin.

FIG. 3D shows γ-irradiation induced DNA damage promotes Htt cleavage in MESC2.10 neurons. γ-irradiation was carried out using a MARK-I γ-irradiator with a $^{137}$Cs source at a specific dose rate of 1.22 Gy/min. Cells were irradiated with 5 Gy and further incubated for the indicated time. Sodium salicylate (NaSal, lane 5) was added at a concentration of 5 mg/ml 1 hour prior to irradiation and incubated for 6 hours. Etoposide treatment (10 μM) was used as a positive control and was carried out for 6 hour (lane 6). Lanes 7 and 8 represent MESC2.10 neurons transduced with an IKKβ shRNA lentivirus (FIG. 4A) and irradiated with 5 Gy and incubated for 6 hours. The asterisk shows full-length Htt and the arrow indicates the cleaved products. Tubulin was used as a loading control

FIG. 4A is a western blot showing a specific anti-IKKβ shRNA inhibits expression of IKKβ. MESC2.10 neurons were transduced with a control or lentivirus expressing specific anti-IKKβ shRNA. The level of IKKβ protein was examined by western blotting with an anti-IKKβ antibody. Bottom panel shows staining of same blot for α-tubulin.

FIG. 4B shows inhibition of etoposide-induced Htt cleavage by silencing of IKKβ. Control or MESC2.10 neurons with silenced IKKβ were treated with etoposide for 6 hours and examined for Htt cleavage (lanes 1 and 2) as described in FIG. 3A. Arrowhead indicates position of full length Htt, and the arrow shows the position of the major cleaved product. The second panel shows IKKγ levels used as a loading control.

FIG. 4C shows DNA binding activity of P65 NF-κB is increased by etoposide and is suppressed by IKKα. Lanes 1-4 show p65 binding from nuclear extracts of control and lanes 5-8 show p65 binding from neurons transduced with a lentivirus expressing IKKα (FIG. 3C). Bars indicate S.E.M. and asterisk shows significant difference between control and IKKα+ neurons treated with etoposide for 4 hour, P<0.01 using a student's t test.

FIG. 4D shows competition of etoposide-induced p65 NF-κB binding by consensus oligonucleotides. Nuclear extracts of etoposide treated neurons were pre-incubated with 100 ng of competitor NF-κB oligonucleotides (Clontech) on ice for 1 hour (Column 3) before treatment with etoposide for 6 hours.

Wells with mutated NF-κB DNA oligonucleotides were used to ensure specificity of the binding (column 4).

Figure 4:
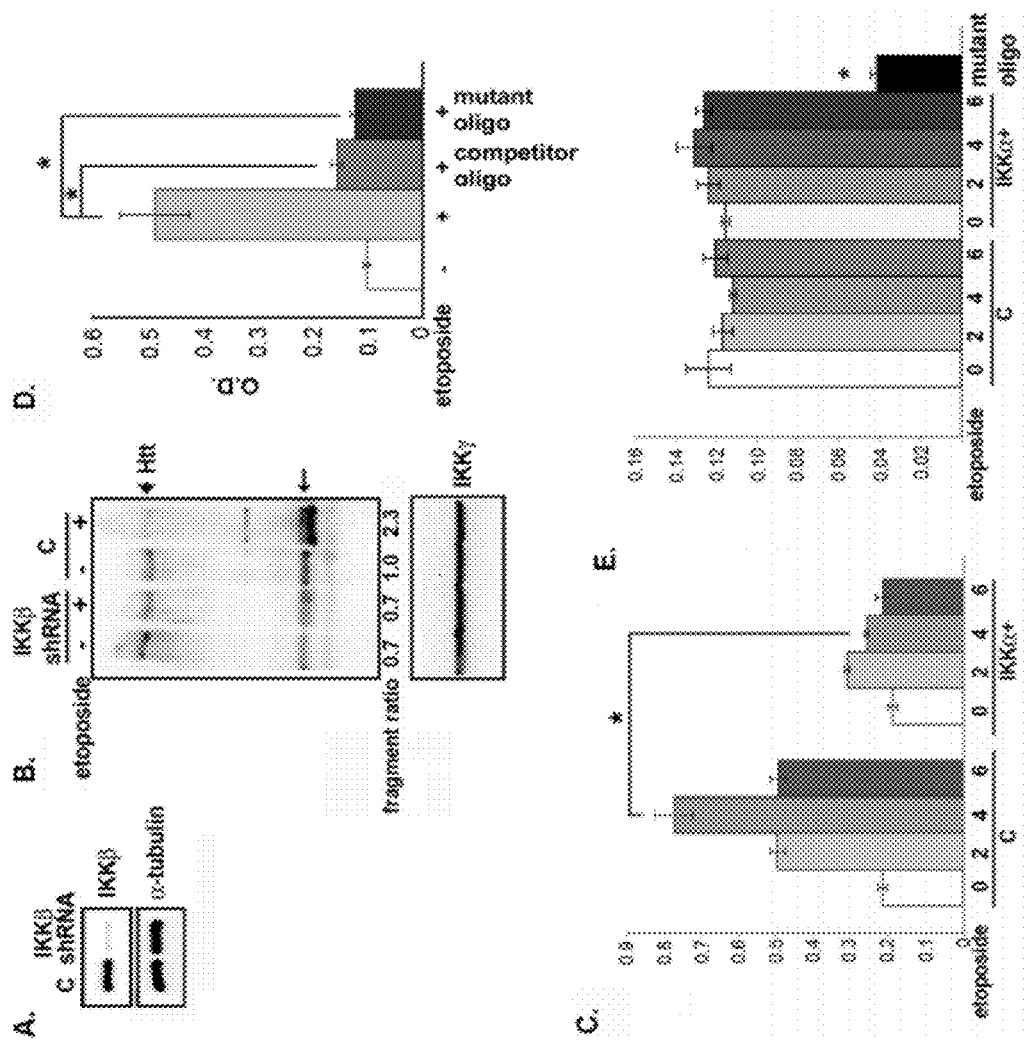
FIGS. 4A-4E show inhibition of IKKβ prevents proteolysis of Htt induced by etoposide.

FIG. 4E shows binding of p52 NF-κB to consensus oligonucleotides is not changed by DNA damage. Experiments were similar to in FIG. 4C, except binding was examined for p52. Bars indicate S.E.M. and asterisks show significant difference in binding between samples without or with the competitor oligonucleotides or with p65 binding to mutated NF-κB oligonucleotides, P value <0.01, using a student's t test.

Figure 5:
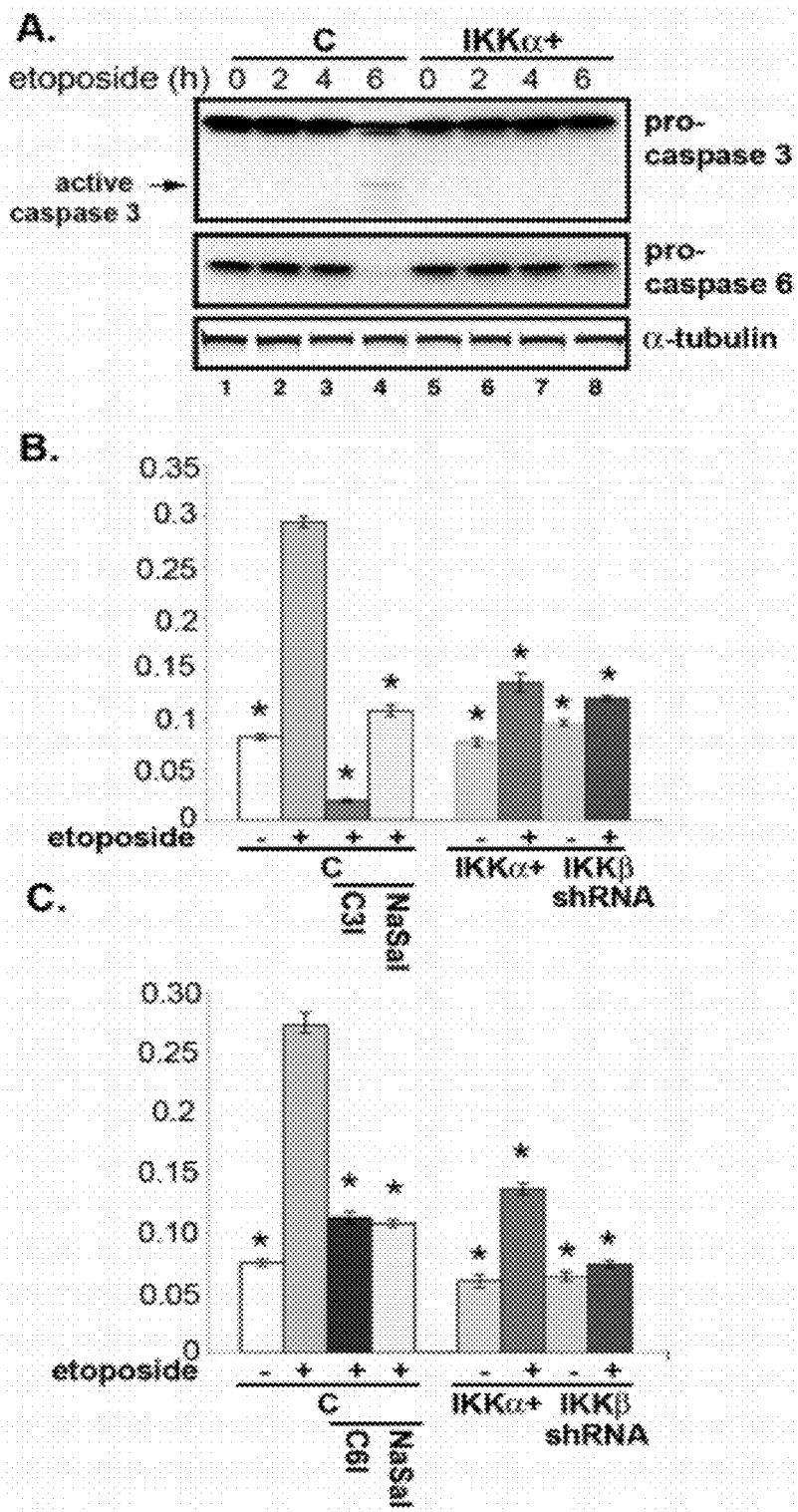

FIGS. 5A-5C show IKKs influence etoposide-induced activation of caspases.

FIG. 5A is a western blot showing activation of caspase-3 and caspase-6. MESC2.10 neurons were treated with etoposide as in FIG. 3A and examined for the levels of procaspase-3 (top panel) or procaspses-6 (middle panel) by western blotting. Arrow shows the cleaved products of procaspase-3.

FIGS. 5B and 5C are graphs showing activities of caspase-3 (FIG. 5B) and caspase-6 (FIG. 5C) activities in MESC2.10 neuronal lysates. For the specific inhibitors, neurons were first pretreated with 20 μM of Ac-DEVD-CHO (caspase-3 inhibitor (C3I) or 20 μM of Ac-VEID-CHO (caspase-6 inhibitor (C6I), or 5 mg/ml of sodium salicylate (NaSal) one hour prior to etoposide treatment for 6 hours. Extracts were incubated with either caspase-3 substrate (DEVD conjugated to p-nitroanaline) or caspase-6 substrate (VEID conjugated to p-nitroanline) in a 96 well plate at 37° C. for 1 hour. Enzyme activities for caspase-3 (FIG. 5B) or caspase-6 (FIG. 5C) were measured in a microplate reader. Results are shown as relative enzyme activity and represent averages of three experiments. Bars indicate S.E.M. and asterisk shows significant difference from etoposide treated control neurons (column 2), p<0.01, using a student's t test.

Figure 6:
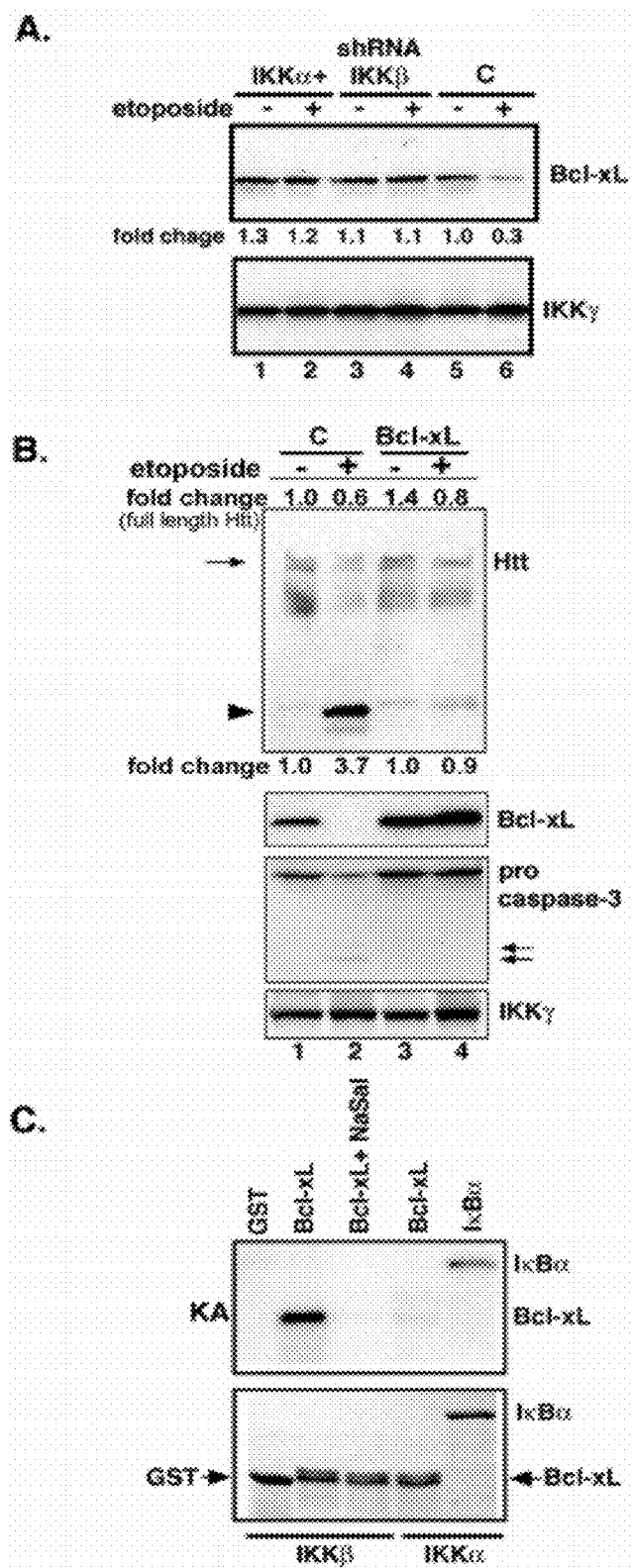

FIGS. 6A-6C show etoposide promotes reduction of Bcl-xL.

FIG. 6A is a western blot showing the expression of Bcl-XL. Extracts of control and etoposide-treated MESC2.10 neurons were examined for Bcl-xL by Western blotting. Neurons were treated with etoposide for 6 hours. Top panel shows staining for Bcl-xL and the bottom panel indicates IKKγ as a loading control. Fold changes were normalized to the intensity of loading control, and compared to that of untreated control neurons (lane 5).

FIG. 6B shows Bcl-xL expression prevents etoposide-induced Htt proteolysis. MESC2.10 neuroblasts were transduced with a lentivirus expressing Bcl-xL (Lanes 3 and 4) and treated with etoposide for 6 hours. EGFP-lentivirus was used a control (C). Top panel Western shows blotting for Htt. Arrow indicates the full-length Htt and the arrowhead shows the cleaved Htt products. Second and third panels show staining for Bcl-xL and pro-caspase-3, respectively. IKKγ levels were used as a loading control.

FIG. 6C shows IKKβ phosphorylates Bcl-xL. Active recombinant IKKα or IKKβ were tested for the ability to phosphorylate Bcl-xL. The kinase assay was performed using recombinant Bcl-xL as a substrate. Products were visualized by autoradiography. IκBα was used as a positive control substrate for IKKα. The top panel shows the kinase product (KA) and bottom panel shows the SDS-PAGE and coomassie-blue staining of the substrates use in kinase assays.

Figure 7:
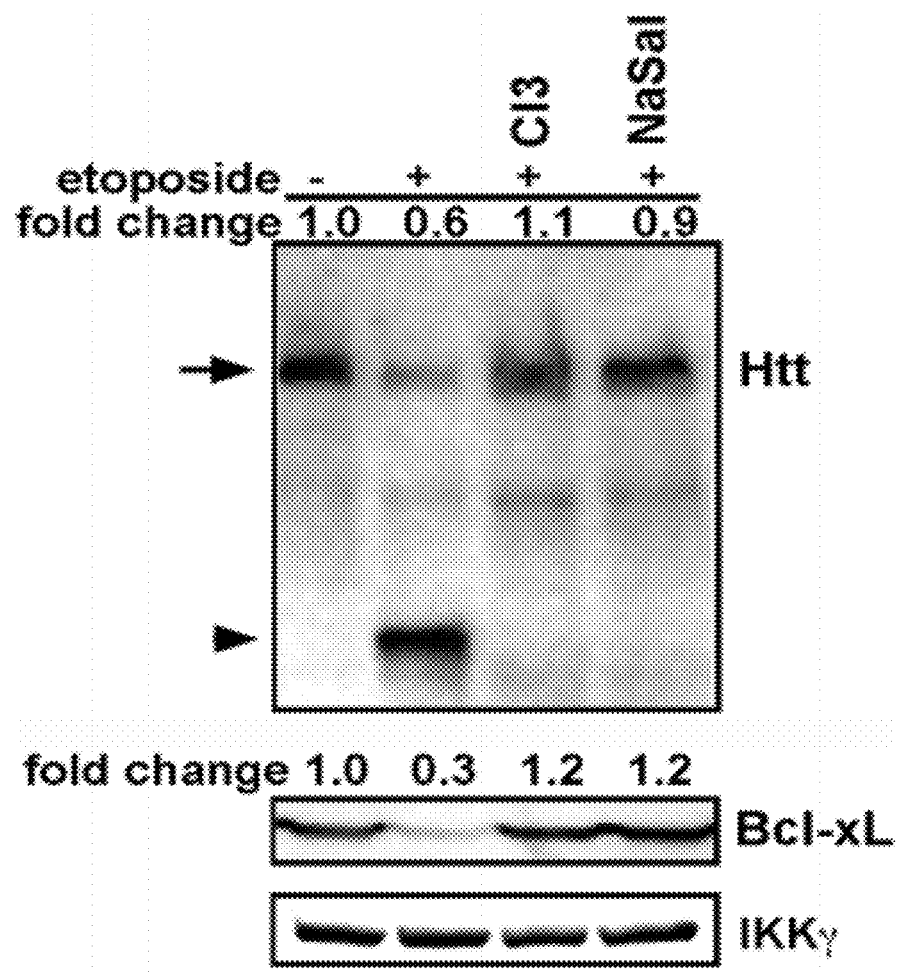

FIG. 7 shows etoposide induces proteolysis of endogenous mutant Htt in neurons striatal (Hdh$^{Q111/Q111}$) neurons. The caspase-3 inhibitor (C3I, 20 μM) and sodium salicylate (NaSal, 5 mg/ml) were added 1 hour prior to the addition of 10 μM etoposide for 6 hours. Processing of samples was as described in FIG. 3A. Top panel shows western blot analysis of lysates for Htt. Arrow indicates the full-length Htt and the arrowhead shows the cleaved Htt products (~90 kDa). The second panel shows the level of Bcl-xL. IKKγ was used as loading control.

Figure 8:
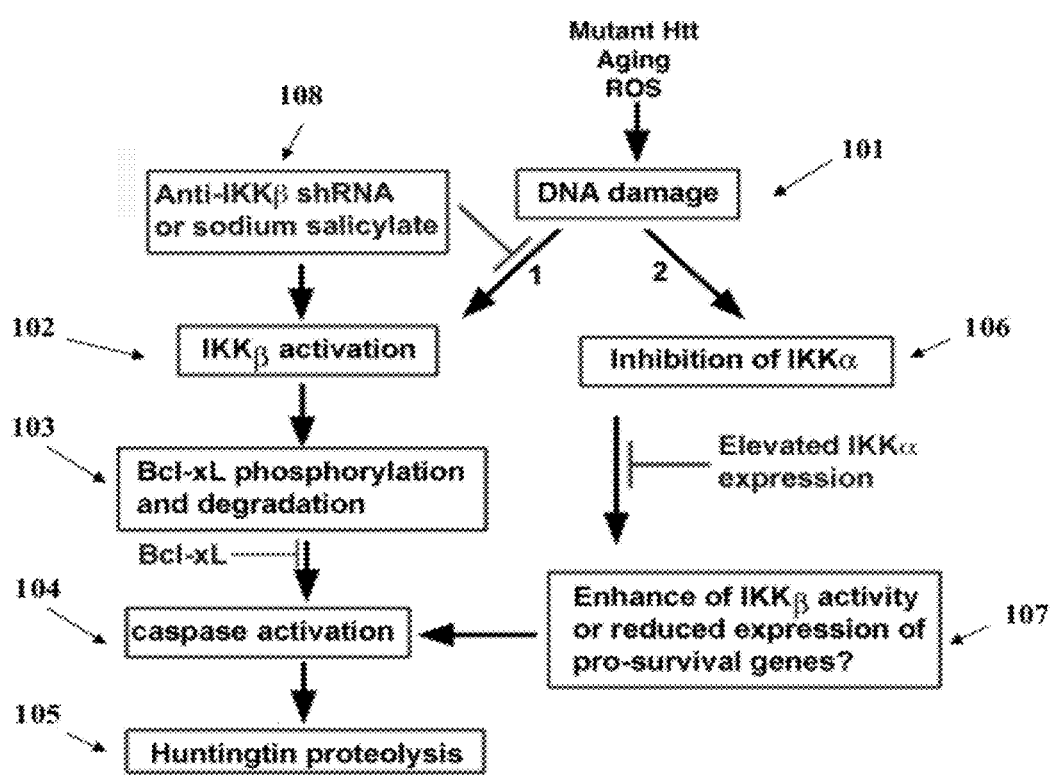
Figure 8:
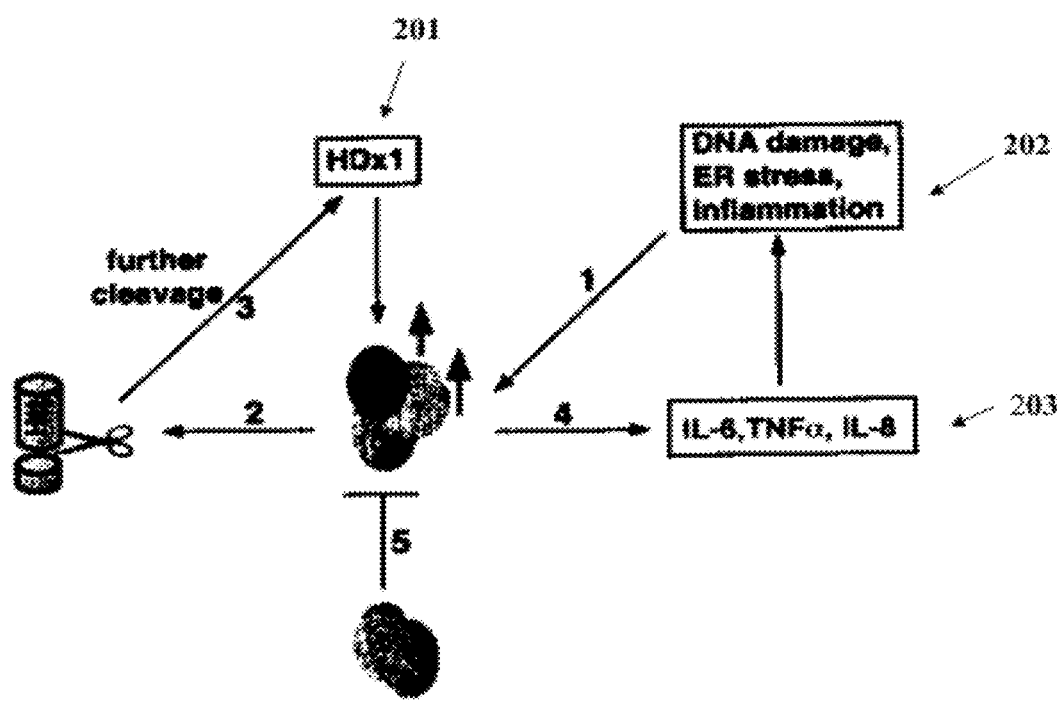

FIG. 8A is a schematic diagram showing a potential signaling pathway for IKKβ-mediated Htt proteolysis in MESC2.10 neurons. DNA damage activates IKKβ, which can phosphorylate Bcl-xL and enhance its degradation (arrow 1). Reduction of Bcl-xL levels triggers the activation of caspases, which cleaves Htt. IKKβ inhibition block degradation of Bcl-xL, caspases activation, and proteolysis of Htt. Similar to the inhibition of IKKβ, elevation of Bcl-xL also prevents caspase activation and Htt proteolysis. On the other hand, etoposide treatment reduces the activity of IKKα (arrow 2). This can enhance IKKβ activation and/or block expression of neuroprotective proteins that are essential for interfering with caspase activation and maintaining Htt levels. Elevated IKKα expressed from a lentivirus overcomes these deficiencies and prevents Htt proteolysis.

FIG. 8B depicts an embodiment of a toxic feedback loop for IKKβ activation and Htt proteolysis. IKKβ can be activated by stress that can promote Htt cleavage. Reduction of WT Htt can impair neuronal function and survival. Cleavage of mutant Htt however, can generate exon-1 like (HDx1) or other small fragments that can also activate IKKβ. This cycle can also be exacerbated by cytokines. This cycle can be suppressed by IKKα.

Figure 9:
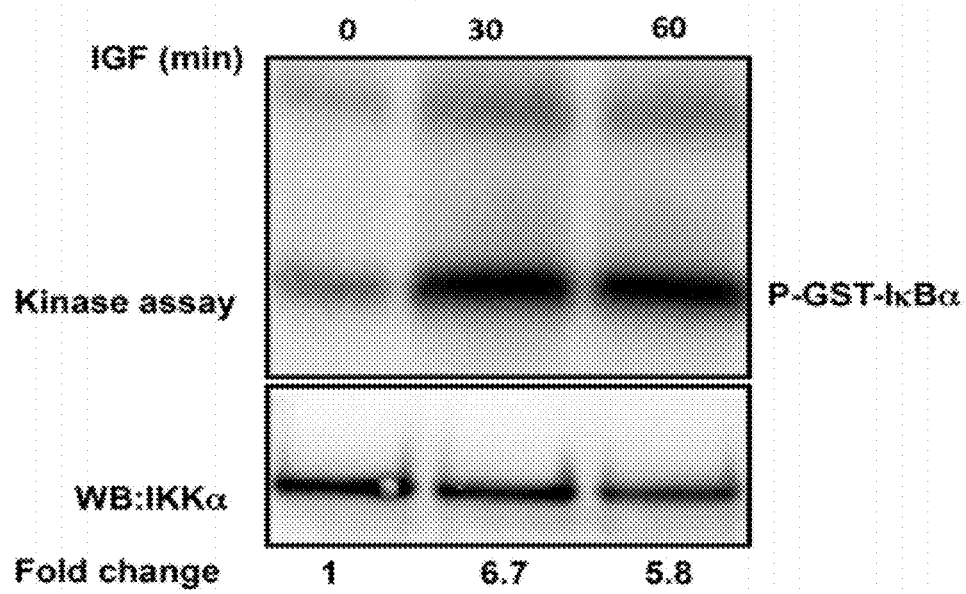
Figure 9:
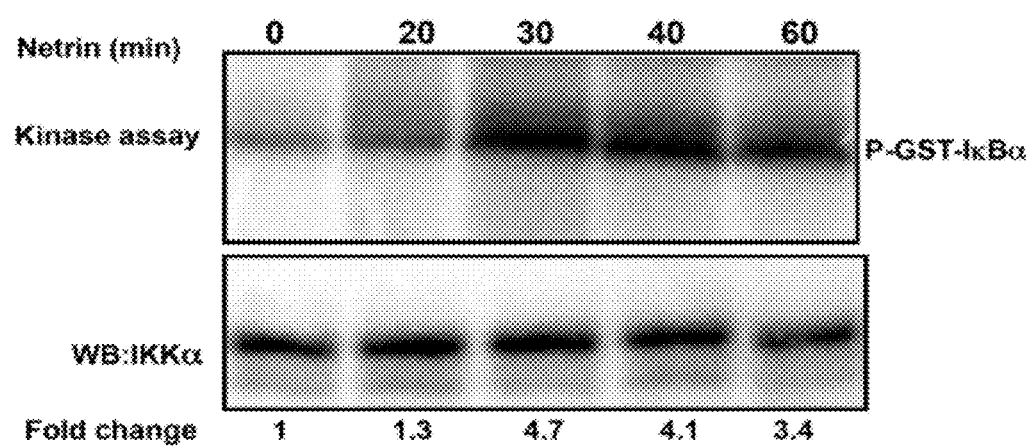

FIGS. 9A & 9B show activation of IKKα by IKKα activators.

FIG. 9A shows insulin-like growth factor-1 (IGF-1) activates IKKα in differentiated neurons. IGF-1 was added at 20 ng/ml for the indicated time.

FIG. 9B shows Netrin activates IKKα in differentiated neurons. Netrin was added at 100 ng/ml for the indicated time.

Figure 10:
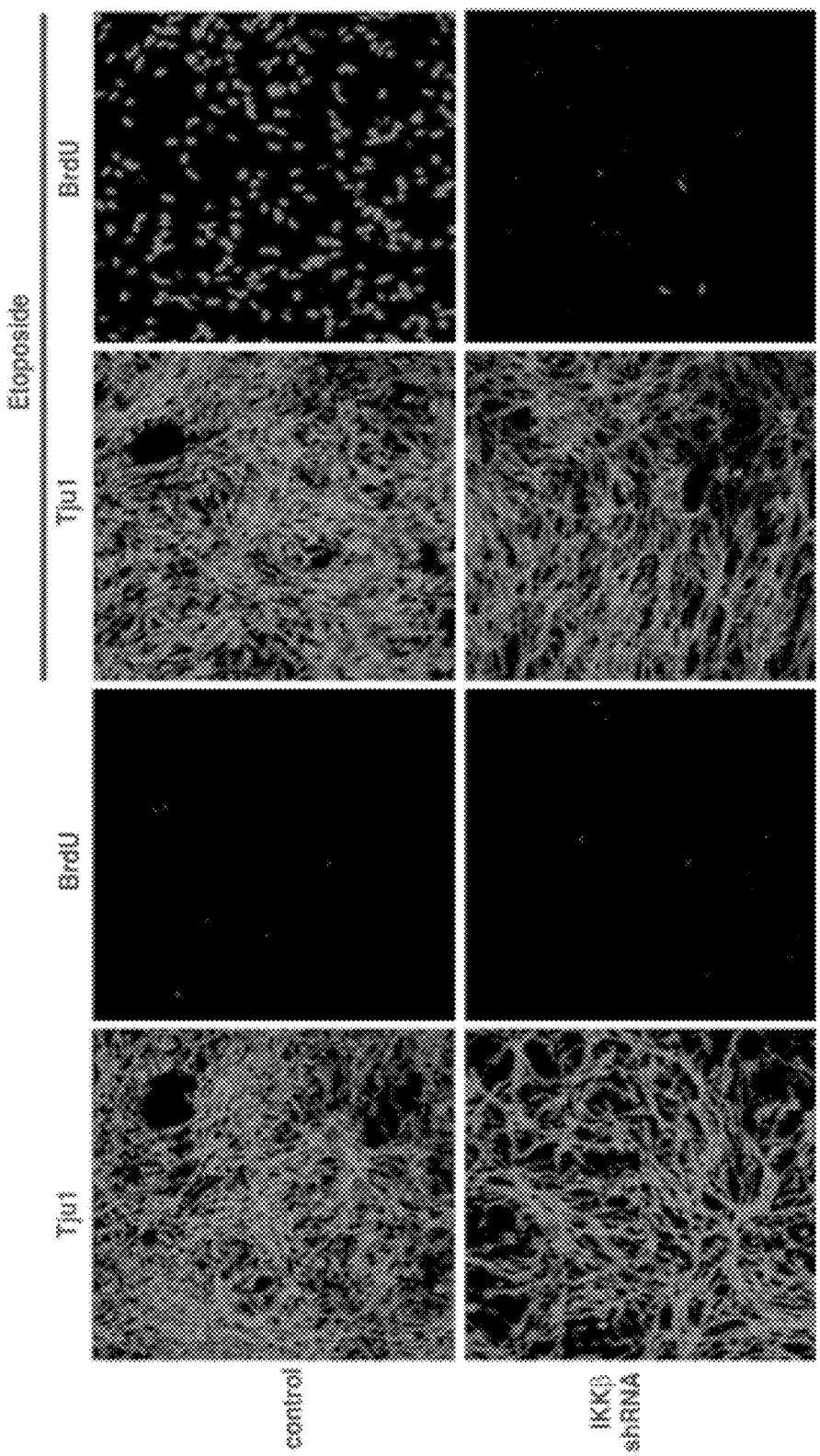

FIG. 10 is a depiction of the confocal microscope images demonstrating that inhibition of IKKβ prevents etoposide-induced BrdU incorporation in MESC2.10 Neurons. BrdU incorporation demonstrates aberrant activation of cell cycle, which leads to neuronal death and that is inhibited by silencing of IKKβ expression. Day 6 differentiated neurons on coverslips were treated with 10 μM etoposide for 4 hrs in the presence of BrdU (1 mM). BrdU incorporation was detected described in M&M. Image was captured with a confocal microscope.

DETAILED DESCRIPTION OF THE PREFERRED EMBODIMENT

As disclosed herein, DNA damage can induce the proteolysis of Htt. In some embodiments, activation of IKK plays a role. Treatment of neurons with the DNA damaging agent (such as etoposide or appropriate irradiation) promotes cleavage of wild type (WT) and mutant Htt, generating N-terminal fragments of 80-90 kDa. This event involves IKKβ and is suppressed by IKKα. Elevated levels of IKKα, or inhibition of IKKβ expression by a small hairpin RNA (shRNA) or its activity by sodium salicylate, reduces Htt proteolysis and increases neuronal resistance to DNA damage. Moreover, IKKβ phosphorylates the anti-apoptotic protein Bcl-xL, a modification known to reduce Bcl-xL levels, and activates caspases that can cleave Htt. When IKKβ expression is blocked, etoposide treatment does not decrease Bcl-xL and activation of caspases is diminished. Similar to silencing of IKKβ, increasing the level of Bcl-xL in neurons prevents etoposide-induced caspase activation and Htt proteolysis. These results indicate that DNA damage triggers cleavage of Htt and identify IKKβ as a prominent regulator. Moreover, IKKβ-dependent reduction of Bcl-xL is important in this process. Thus, inhibition of IKKβ, inhibition of caspases, activation of IKKα, and activation of Bcl-xL promote neuronal survival in Huntington's Disease (HD) as well as other DNA damage-induced neurodegenerative disorders.

In some aspects, the present application relates to methods for screening for a compound useful for protecting cells from DNA damage-induced Htt proteolysis. In some embodiments, the compound is an Htt proteolysis inhibitor. In some embodiments, the Htt proteolysis inhibitor is an IKKβ inhibitors. In some embodiments, the Htt proteolysis inhibitor is a caspase inhibitor. In some embodiments, the Htt proteolysis inhibitor is an IKKα activator. In some embodiments, the Htt proteolysis inhibitor is a Bcl-xL inducer. In some embodiments, the Htt proteolysis inhibitors can be used for treating an Htt proteolysis related disorder (such as, for example, HD).

In some embodiments, a method of identifying a compound for protecting a cell from DNA damage-induced Htt proteolysis is provided, where the method comprises: providing one or more compounds to be tested; identifying which compound is an IKKβ inhibitor; and testing the compound identified as the IKKβ inhibitor for its ability to reduce the cleavage of Htt. The Htt can be wild type Htt and/or mutant Htt. In some embodiments, the compound can be a small molecule, a nucleic acid, a peptide, and/or an antibody. In some embodiments, the cell can be a neuron. In some embodiments, the ability of the compound to reduce the cleavage of Htt can be tested by monitoring a cell's survival or by directly monitoring the cleaved Htt product. In some embodiments, identifying the IKKβ inhibitor comprises testing a compound for its ability to inhibit or reduce the ability of IKKβ to phosphorylate a substrate, for example, Bcl-xL. In other embodiments, identifying the IKKβ inhibitor comprises testing a compound for its ability to inhibit or reduce activation of one or more caspases, preferably the caspases that can cleave Htt, such as caspase-3 and caspase-6.

In some embodiments, a method of identifying a compound for protecting a neuronal cell from a DNA damage-induced neurodegenerative disorders is provided, where the method comprises: providing one or more compounds to be tested, inducing DNA damage in a neuronal cell, and testing the compound for its ability to reduce the cleavage of Htt that results from the induced DNA damage in the neuronal cell. The Htt can be wild type Htt and/or mutant Htt. In some embodiments, the compound can be a small molecule, a nucleic acid, a peptide, and/or an antibody. In some embodiments, the cell can be a neuron. In some embodiments, the ability of the compound to reduce the cleavage of Htt can be tested by monitoring a cell's survival or by directly monitoring the cleaved Htt product. In some embodiments, one can also perform the process of identifying the compound as any of an IKKβ inhibitor, a Bcl-xL inducer, an IKKα activator, or some combination thereof. In some embodiments, the process can include testing a compound for its ability to inhibit or reduce the ability of IKKβ to phosphorylate a substrate, for example, Bcl-xL. In some embodiments, identifying the IKKβ inhibitor comprises testing a compound for its ability to inhibit or reduce activation of one or more caspases, preferably the caspases that can cleave Htt, such as caspase-3 and caspase-6.

In other embodiments, a method for identifying a compound for protecting a cell from DNA damage-induced Htt proteolysis is provided, where the method comprises: providing one or more compounds to be tested; identifying which compound is selected from the group consisting of IKKα activator, Bcl-xL inducer, and some combination thereof; and testing the compound identified as an IKKα activator, a Bcl-xL inducer, or some combination thereof for its ability to reduce the cleavage of Htt. The Htt can be wild type Htt or mutant Htt. In some embodiments, the cell can be a neuron. In some embodiments, the compound can be a small molecule, a nucleic acid, a peptide, and/or an antibody. In some embodiments, the ability of the compound to reduce the cleavage of Htt can be tested by monitoring a cell's survival or through directly monitoring the cleaved Htt product. In some embodiments, identifying the IKKα activator the Bcl-xL inducer, or some combination thereof, comprises testing a compound for its ability to inhibit or reduce the phosphorylation and/or degradation of Bcl-xL. In other embodiments, identifying the IKKα activator, a Bcl-xL inducer, or some combination thereof comprises testing a compound for its ability to inhibit activation of one or more caspases, preferably the caspases that can cleave Htt, such as caspase-3 and caspase-6. In still other embodiments, identifying the Bcl-xL inducer comprises testing a compound for its ability to inhibit or reduce the phosphorylation and/or degradation of Bcl-xL.

In another aspect, the present application relates to a method for protecting at least one cell from DNA damage. In some embodiments, the method comprises: inhibiting DNA damage-induced Htt proteolysis in at least one cell by contacting at least one cell with at least one Htt proteolysis inhibitor. Compounds that are Htt proteolysis inhibitors include, but are not limited to, small molecules, nucleic acids, peptides, and antibodies. Compounds that inhibit Htt proteolysis and thus suitable for use in the method disclosed herein for protecting at least one cell from DNA damage include, but are not limited to, IKKβ inhibitors, IKKα activators, Bcl-xL inducers, and caspase inhibitors.

In some embodiments, the at least one Htt proteolysis inhibitor can be an IKKβ inhibitor. Examples of the IKKβ inhibitor include, but are not limited to herbimycin, sodium salicylate, retinoid-related compounds, cyclopentenone prostaglandins, anti-IKKβ small hairpin RNA (shRNA), and NF-κB essential modulator (NEMO) binding peptide, IKKα, BMS-345541 (4(2'-aminoethyl)amino-1,8-dimethylimidazo (1,2-a)quinoxaline), tricyclic based inhibitors of IKK (for example, oxazole-based IKK inhibitors, thiazole-based IKK inhibitors and imidazole-based IKK inhibitors), and some combination thereof.

In some embodiments, the at least one Htt proteolysis inhibitor can be an IKKα activator. Examples of IKKα activators include, but are not limited to, IGF, netrin, and some combination thereof.

In some embodiments, at least one Htt proteolysis inhibitor can be a Bcl-xL inducer. Examples of Bcl-xL inducers include, but are not limited to, IKKα, tea polyphenol, epigallocatechin gallate (EGCG), Bcl-xL, IGFs (for example IGF-1 and IGF-2); brain-derived neurotrophic factor (BDNF); cystamine, memantine, and some combination thereof.

In some embodiments, the at least one Htt proteolysis inhibitor can be a caspase inhibitor. Examples of caspase inhibitors include, but are not limited to, broad-spectrum caspase inhibitors including, but not limited to BOC-D-FMK, Z-VAD-FMK and Q-VD-OPH; caspase-3/7 inhibitor Z-DEVD-FMK; caspase-3 inhibitor Ac-DEVD-CHO; caspase-6 inhibitor Ac-VEID-CHO; and caspase-9 inhibitor Z-LEHD-FMK.

In some aspects, the present application relates to a kit for screening IKKα activator. In some embodiments, the kit comprises a control IKKα activator and a means for monitoring DNA damage-induced Htt proteolysis.

In some aspects, the present application discloses a method for treating a Htt proteolysis related disorder (such as HD). In some embodiments, the method comprises administering a therapeutically effective amount of at least one Htt proteolysis inhibitor to a patient. In some embodiments, the at least one Htt proteolysis inhibitor can block the cleavage of wild type and/or mutant Htt. In other embodiments, at least one Htt proteolysis inhibitor can reduce the cleavage of wildtype and/or mutant Htt.

DEFINITIONS

Unless defined otherwise, technical and scientific terms used herein have the same meaning as commonly understood by one of ordinary skill in the art to which this invention belongs. See e.g., Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present application, the following terms are defined below.

As used herein, "Huntingtin" and "Htt" refer broadly to the huntingtin gene and the protein encoded by the huntingtin gene, including mutant and variant forms as well as native (or wild type ("WT") forms. "Variants" are biologically active polypeptides having an amino acid sequence which differs from the sequence of a native sequence polypeptide. Native sequence human huntingtin protein is described, for example, by The Huntington's Disease Collaborative Research Group in Cell 72:971-983 (1993) as well as in Li et al. Nature 378:398-402 (1995) and WO 02/29408. The number of polyglutamine repeats in native huntingtin protein is known to vary, from about 13 to about 36 glutamine residues in the polyQ region of native human protein. Native sequence murine Htt is described, for example, in Lin et al. Hum. Mol. Genet. 3 (1), 85-92 (1994) and typically comprises about 7 glutamine residues in the polyQ region. Particular variants of the huntingtin gene will comprise different numbers of CAG repeats, resulting in variation in the polyglutamine region of the huntingtin protein.

As used herein, "mutant huntingtin protein" refers to huntingtin protein which differs in some respect from the native sequence huntingtin protein. Typically, mutant Htt will comprise an expanded polyglutamine region compared to the native form. A preferred mutant Htt has an expanded polyglutamine region of 40 or more glutamine residues.

As used herein, "IKK" refers broadly to the Iκ-B kinase (IKK) complex. DNA damage is a potent inducer of IKK. The core Iκ-B kinase complex has two kinase catalytic subunits IKKα and IKKβ, and a regulatory subunit IKKγ. Both IKKα and IKKβ can catalyze the phosphorylation of Iκ-B protein, but IKKβ is mainly responsible for the activation of NF-κB by pro-inflammatory stimuli and DNA damage.

As used herein, the term "Htt proteolysis inhibitor" (or "HPI") is used in the broadest sense and includes any molecule that partially or fully blocks, inhibits, or reduces the proteolysis of Htt. Htt proteolysis inhibitors can be in various forms, including, but not limited to, small molecules, nucleic acids, peptides, and antibodies. Unless specified, the way by which Htt proteolysis inhibitors block or reduce the cleavage of Htt is not limited in anyway. Htt proteolysis inhibitors can have various modes of action. In some embodiments, an Htt proteolysis inhibitor can be an IKKβ inhibitor. In some embodiments, an Htt proteolysis inhibitor can be an IKKα activator. In some embodiments, an Htt proteolysis inhibitor can be a caspase inhibitor. In some embodiments, an Htt proteolysis inhibitor can be a Bcl-xL inducer. In some embodiments, the inhibition is at least 5%, for example, at least any of the following: 5, 10, 15, 20, 25, 30, 35, 40, 45, 50, 55, 60, 65, 70, 75, 80, 85, 90, 91, 92, 93, 94, 95, 96, 97, 98, 99, 99.9 percent or greater inhibition, including any range above any of the previous values and any range defined between any of the two previous values.

As used herein, the term "HP protein" refers to any protein that is involved in the Htt proteolysis pathway. Non-limiting examples of HP proteins include IKKβ, caspases (such as caspase-3 and caspase-6), IKKα, and Bcl-xL. The term "HP gene" refers to any gene that encodes a protein involved in the Htt proteolysis pathway. HP genes include, but are not limited to, IKKβ gene, caspase genes (such as caspase-3 gene and caspase-6 gene), IKKα gene, and Bcl-xL gene.

As used herein, the term "IKKβ inhibitor" is used in the broadest sense and includes any molecule that partially or fully blocks, inhibits or neutralizes a biological activity mediated by IKKβ, preferably by preventing or reducing the activation of IKKβ or phosphorylation activity of IKKβ. The term "IKKβ inhibitor" also includes any molecule that mimics a biological activity mediated by IKKβ and specifically changes, preferably abolishes or reduces, the function or expression of IKKβ, or the efficiency of signaling through IKKβ. In some embodiments, the inhibition is at least 5%, for example, at least any of the following: 5, 10, 15, 20, 25, 30, 35, 40, 45, 50, 55, 60, 65, 70, 75, 80, 85, 90, 91, 92, 93, 94, 95, 96, 97, 98, 99 percent or greater inhibition, including any range above any of the previous values and any range defined between any of the two previous values.

As used herein, the term "IKKα activator" is used in the broadest sense and includes any molecule that partially or fully activates a biological activity mediated by IKKα. The term "IKKα activator" also includes any molecule that mimics a biological activity mediated by IKKα and specifically changes, preferably increases, the function or expression of IKKα, or the efficiency of signaling through IKKα. In some embodiments, the activation is at least 5%, for example, at least any of the following: 5, 10, 15, 20, 25, 30, 35, 40, 45, 50, 55, 60, 65, 70, 75, 80, 85, 90, 91, 92, 93, 94, 95, 96, 97, 98, 99, 100, 110, 150, 200, 300, 400, 500, 1000, 2000, 10,000, percent or greater activation, including any range above any of the previous values and any range defined between any of the two previous values. Anything that increases the level of IKKα can also be called an IKKα activator. Thus, in some embodiments, additional IKKα protein or a gene that encodes for IKKα can also be an IKKα activator as the term is used herein.

As used herein, the term "caspase inhibitor" is used in the broadest sense and includes any molecule that partially or fully blocks, inhibits or neutralizes a biological activity mediated by one or more caspases, preferably by preventing or reducing the activation of the caspase(s) or the proteolytic activity of the caspase(s). The term "caspase inhibitor" also includes any molecule that mimics a biological activity mediated by IKKβ and specifically changes, preferably abolishes or reduces, the function or expression of one or more caspases, or the efficiency of caspase cleavage. In some embodiments, the inhibition is at least 5%, for example, at least any of the following: 5, 10, 15, 20, 25, 30, 35, 40, 45, 50, 55, 60, 65, 70, 75, 80, 85, 90, 91, 92, 93, 94, 95, 96, 97, 98, 99 percent or greater inhibition, including any range above any of the previous values and any range defined between any of the two previous values.

As used herein, the term "Bcl-xL inducer" is used in the broadest sense and includes any molecule that partially or fully activates a biological activity mediated by Bcl-xl. The term "Bcl-xL inducer" also includes any molecule that mimics a biological activity mediated by Bcl-xl and specifically changes, preferably increases, the function or expression of Bcl-xl. Bcl-xL inducers can also prevent or reduce the phosphorylation of Bcl-xl, or the degradation of Bcl-xL. In some embodiments, the activation is at least 5%, for example, at least any of the following: 5, 10, 15, 20, 25, 30, 35, 40, 45, 50, 55, 60, 65, 70, 75, 80, 85, 90, 91, 92, 93, 94, 95, 96, 97, 98, 99, 100, 110, 150, 200, 300, 400, 500, 1000, 2000, 10,000, percent or greater activation, including any range above any of the previous values and any range defined between any of the two previous values. Anything that increases the level of Bcl-xl can also be called an Bcl-xL inducer. Thus, in some embodiments, additional Bcl-xl protein or a gene that encodes for Bcl-xl can also be a Bcl-xL inducer, as the term is used herein.

A used herein, "biological property" or "biological activity" is a biological function caused by IKKβ, IKKα, Bcl-xL, caspases, an IKKβ inhibitor, an IKKα activator, a Bcl-xL inducer, a caspase inhibitor, or other compounds disclosed in the present application. For example, biological properties of IKKβ include, but are not limited to, the phosphorylation of Bcl-xL, promoting degradation of Bcl-xL, inducing activation of various caspases such as caspase-3 and caspase-6, phosphorylation of I-κB, and activation of NF-κB dependent pathways. Biological properties of IKKα include, but are not limited to, inhibiting activation of IKKβ, preventing or reducing phosphorylation and/or degradation of Bcl-xL, inhibiting activation of various caspases such as caspase-3 and caspase-6, and protecting cells from DNA damage-induced Htt proteolysis. Biological properties of Bcl-xL include, but are not limited to, preventing or reducing activation of caspases such as caspase-3 and caspase-6 and preventing or reducing cleavage of wild type and/or mutant Htt. Biological properties of caspases include, but are not limited to, cleaving protein substrates such as wild type and mutant Htt. In some embodiments, the property or activity is that noted in FIG. 8.

With regard to IKKβ inhibitors, biological activity refers, in part, to the ability to inhibit activation of IKKβ. Other preferred biological activities of IKKβ inhibitors include prevention of cell death or apoptosis, inhibition of phosphorylation and/or degradation of Bcl-xL, inhibition of activation of caspases such as caspase-3 and caspase-6, inhibition of NF-κB dependent gene transcription and the ability to regulate and preferably reduce or eliminate the DNA damage-induced Htt proteolysis that are associated with neurodegenerative diseases.

With regard to IKKα activators, biological activity refers, in part, to the ability to promote activation of IKKα. Other preferred biological activities of IKKα activators include prevention of cell death or apoptosis, inhibition of phosphorylation and/or degradation of Bcl-xL, inhibition of activation of caspases such as caspase-3 and caspase-6, and the ability to regulate and preferably reduce or eliminate the DNA damage-induced Htt proteolysis that are associated with neurodegenerative diseases.

With regard to caspase inhibitors, biological activity refers, in part, to the ability to inhibit activation of one or more caspases, preferably caspase-3 and caspase-6. Other preferred biological activities of caspase inhibitors include prevention of cell death or apoptosis, inhibition of DNA damage-induced Htt proteolysis, and the ability to regulate and preferably reduce or eliminate the DNA damage-induced Htt proteolysis that are associated with neurodegenerative diseases.

With regard to Bcl-xL inducers, biological activity refers, in part, to the ability to inhibit or reduce the activation of one or more caspases, preferably caspase-3 and caspase-6. Other preferred biological activities of Bcl-xL inducers include prevention of cell death or apoptosis, inhibition of phosphorylation and/or degradation of Bcl-xL, inhibition of activation of caspases such as caspase-3 and caspase-6, and the ability to regulate and preferably reduce or eliminate the DNA damage-induced Htt proteolysis that are associated with neurodegenerative diseases.

As disclosed herein, DNA damage-induced Htt proteolysis can be triggered by any DNA Damage-inducing Agents. Examples of DNA damage-inducing agent include, but are not limited to, a topoisomerase inhibitor (for example, oxorubicin, etoposide, teniposide, sobuzoxane, camptothecin, topotecan, irinotecan, belotecan, or an analogue or derivative thereof), DNA binding agent (for example, DNA minor groove binding agents, DNA crosslinking agents, intercalating agents, and DNA adduct forming agents), anti-metabolite, ionizing radiation (for example, γ-radiation, X-ray radiation and ultraviolet light radiation), virus, hydrolysis or thermal disruption, restriction enzyme, or a combination of two or more of such known DNA damaging agents.

As used herein, the term "therapeutically effective amount" or "therapeutically effective dose" refers to an amount effective to treat a disease or disorder. In the case of HD, the therapeutically effective amount of an IKKβ inhibitor, an IKKα activator, or a Bcl-xL inducer prevents or reduces the risk or immediacy of cell death associated with Htt proteolysis and/or reduces one or more of the symptoms of HD. The therapeutically effective dose can be a single dose, or can comprise multiple doses given over a period of time. In some embodiments, the amount used can be sufficient to lower the cleaved Htt protein in the cell and/or the organism.

As used herein, the term "antibody" is used herein in the broadest sense and specifically covers human, non-human (e.g., murine) and humanized monoclonal antibodies, including, but not limited to, full-length monoclonal antibodies, polyclonal antibodies, multi-specific antibodies, and antibody fragments, including intrabodies, so long as they exhibit a desired biological activity. In general, an antibody exhibits binding specificity to a specific antigen.

As used herein, an "individual" is a vertebrate, preferably a mammal, more preferably a human. "Mammal" for purposes of treatment refers to any animal classified as a mammal, including humans, domestic and farm animals; and zoo, sports, or pet animals, such as dogs, horses, cats, cows, etc. Preferably, a mammal is human.

As used herein, "treatment" is a clinical intervention made in response to and in anticipation of a disease, disorder or physiological condition manifested by a patient, particularly HD. The aim of treatment includes the alleviation or prevention of one or more symptoms, slowing or stopping the progression or worsening of a disease, disorder, or condition and/or the remission of the disease, disorder or condition. "Treatment" refers to both therapeutic treatment and prophylactic or preventative measures. Those in need of treatment include those already affected by a disease or disorder or undesired physiological condition as well as those in which the disease or disorder or undesired physiological condition is to be prevented.

In the methods of the present application, the term "control" and grammatical variants thereof, refer to the prevention, partial or complete inhibition, reduction, delay or slowing down of an unwanted event, such as the presence or onset of HD.

The term "DNA damaging agent" encompasses both materials that result in DNA damage, such as etoposide, oxidative stress, aging, irradiation.

The term "DNA damage induced neurodegeneration disorder" includes those diseases and disorders where neurodegeneration is due to DNA damage. Huntington's disease is one such example, as well as one or more of the following: aging, and other disorders caused by damage to DNA due to exposure to DNA damage-inducing agents, including, without limitation, carcinogens, toxins, free radicals, such as oxygen radicals, or DNA damaging radiations like ionizing radiation and UV radiation. The DNA damage-induced Htt proteolysis-related disorders are associated with dysfunction in Htt proteolysis. Examples of DNA damage-induced Htt proteolysis-related disorders include, but are not limited to, neurodegenerative disorders, such as Huntington's disease (HD), multiple sclerosis, ischemia, Parkinson's disease, Alzheimer's disease, adrenoleukodystrophy (ALD), alcoholism, Alexander's disease, Alper's disease, amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), canavan disease, cockayne syndrome, corticobasal degeneration, Creutzfeldt-Jakob disease, familial fatal insomnia, frontotemporal lobar degeneration, HIV-associated dementia, Kennedy's disease, Krabbe's disease, Lewy body dementia, neuroborreliosis, machado-Joseph disease (Spinocerebellar ataxia type 3), multiple system atrophy, narcolepsy, Niemann Pick disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spinocerebellar ataxia (multiple types with varying characteristics), spinal muscular atrophy. Steele-Richardson-Olszewski disease, tabes dorsalis, toxic encephalopathy; aging and age-related degenerative diseases, such as Ataxia telangiectasia, Bloom syndrome, Cockayne's syndrome, Progeria (Hutchinson-Gilford Progeria syndrome), Rothmund-Thomson syndrome, Trichothiodystrophy, Werner syndrome, and Xeroderma pigmentosum. This can also include oxidative stress and the effects of aging on cells. In some embodiments, the DNA damage induced neurodegeneration disorder can be identified by, and encompasses, disorders where DNA damage results in Htt cleavage. Thus, in some embodiments, such disorders can be readily identified by looking for the amount of wild type or mutant Htt that is cleaved, where there will be elevated levels of cleaved Htt in such DNA damage induced neurodegeneration disorders.

DNA Damage Induced Htt Cleavage

Accumulation of DNA damage as well as activation of modifiers that influence Htt proteolysis can impact disease progression. As disclosed herein, IKKβ is a regulator of enzymes known to cleave Htt in cells. As disclosed herein, IKKβ activation by DNA damage promotes Htt proteolysis by influencing caspase, such as caspase-3 and caspase-6, activity in cells such as post-mitotic neurons. Activation of IKKβ in neurons can trigger Htt proteolysis cell autonomously, as in the case with induction of DNA damage (FIG. 8A), or non-autonomously by chronic exposure to pro-inflammatory cytokines produced by microglia (FIG. 8B).

In contrast to IKKβ, IKKα promotes neuronal survival and prevents Htt proteolysis. This can result from IKKα inhibition of IKKβ, or IKKα can prevent Htt proteolysis independent of IKKβ by modulating expression and/or activation of gene products that antagonize the toxic effects of DNA damage-inducing agents, such as etoposide.

As shown in FIG. 8A, mutant Htt, aging, or reactive oxygen species (ROS) can cause DNA damage 101. DNA damage 101 can induce IKKβ activation 102 in cells (such as neurons). The activation of IKKβ can promote Htt proteolysis 105 indirectly by regulating Bcl-xL levels (FIG. 8A). IKKβ activation 102 can lead to phosphorylation, and thus promote the degradation of Bcl-xL 103. The reduction of Bcl-1xL can be a signal that leads to activation of enzymes that target Htt (such as caspase activation 104), which can cause Htt proteolysis 105.

Inhibition of IKKβ (for example, by anti-IKKβ shRNA or sodium salicylate 108) can prevent Htt proteolysis 105, which includes depletion of wild type Htt as well as the production of toxic N-terminal fragments generated from the cleavage of mutant Htt. The phosphorylation and degradation of Bcl-xL 103 can be inhibited by Bcl-xL itself.

Also shown in FIG. 8A, DNA damage 101 can lead to inhibition of IKKα 106, which can subsequently enhance IKKβ activity or reduce expression of pro-survival genes (as shown in 107). Elevated IKKα expression can block the enhancement of IKKβ activity or reduction of expression of pro-survival genes.

IKKβ is itself activated by N-terminal fragments of mutant Htt. Accordingly, Htt proteolysis and IKKβ activation can form a toxic feedback loop that could promote neurodegeneration (FIG. 8B). This cycle can be influenced by cytokines (such as IL-6, IL-1β, TNFα and IL-8 shown in 203) that are induced by IKKβ activation and are elevated in HD patients. On the other hand, IKKα can act as a break to suppress excessive IKKβ activation and reduce toxicity. Thus, the ratio of IKKα to IKKβ can be a determinant of Htt proteolysis in stressed neurons.

Identification of IKKs as regulators of Htt proteolysis offers a novel strategy for molecules that would prevent one of the earliest events in HD pathogenesis.

Disclosed in the examples below is data identifying IKKβ as a prominent regulator of enzymes known to cleave Htt in stressed human neurons. IKKβ activation by DNA damage promotes Htt proteolysis by influencing caspase-3 activity in post-mitotic neurons (FIG. 8A). The data support a role for caspase-3 in the DNA damage paradigm. While the role of caspase-3-mediated proteolysis of mutant Htt in HD pathology remains unknown, cleavage of WT Htt can impair its vital function in neurons (FIG. 8A).

The disclosed data indicate that DNA damage activation of IKKβ can injure neurons by increasing the turnover of WT Htt and by generating potentially toxic N-terminal fragments of mutant Htt. Activation of IKKβ in neurons can also be mediated by chronic exposure to pro-inflammatory cytokines, which are elevated in the plasma and brain tissue of HD patients. Activation of IKKβ in neurons can trigger Htt proteolysis cell autonomously, as in the case with the induction of DNA damage, or non-autonomously by chronic exposure to proinflammatory cytokines produced by microglia (FIG. 8B). In contrast to IKKβ, IKKα promotes neuronal survival and prevents Htt proteolysis. The mechanism of Htt proteolysis is complex and probably involves integration of multiple signaling pathways. The present results in the below examples identify Bcl-xL as a likely mediator of Htt proteolysis activated by DNA damage. The present results show that etoposide reduces Bcl-xL levels in neurons in an IKKβ-dependent manner. A role for IKKβ is supported by the inability of etoposide to reduce Bcl-xL in neurons expressing an shRNA targeting IKKβ or in neurons pretreated with sodium salicylate, a potent inhibitor of IKKβ. It appears that IKKβ reduces Bcl-xL level by phosphorylation, a modification that promotes Bcl-xL degradation. Phosphorylation-dependent degradation of Bcl-xL is suggested to play a role in spinal cord neuronal injury and is implicated in Htt proteolysis in the striatum of 3-nitropropionic acid injected mice. Thus, reduction of Bcl-xL can be the signal hat leads to activation of enzymes that target Htt (FIG. 8A).

The data presented in the Examples below suggest that DNA damage-induced IKKβ in neurons promotes Htt turnover by regulating Bcl-xL levels (FIG. 8A). Inhibition of IKKβ prevents depletion of WT Htt as well as the production of toxic N-terminal fragments generated from the cleavage of mutant Htt.

Htt Proteolysis Inhibitors

As discussed above, "Htt proteolysis inhibitors" ("HPI") is used herein in a broad sense and includes any molecule that partially or fully blocks, inhibits, or reduces the proteolysis of Htt. In some embodiments, the present application provides methods for screening for Htt proteolysis inhibitors useful for protecting cells from DNA damage-induced Htt proteolysis and for treating HD.

The method by which Htt proteolysis is inhibited is not limited in any way. Htt proteolysis inhibitors can have various modes of action. In some embodiments, an Htt proteolysis inhibitor acts directly on Htt, for example by binding to Htt, to prevent Htt proteolysis. In some embodiments, an Htt proteolysis inhibitor can act directly on one or more proteases that can cleave Htt, for example by binding to the protease(s) to prevent the protease from interacting with its substrate, such as Htt. Examples of proteases that can cleave Htt include, but are not limited to, caspases (for example caspase-3, caspase-6 and caspase-9), calpains (for example, calpain-1, calpain-3, calpain-5, and calpain-10) and apopain. In some embodiments, an Htt proteolysis inhibitor can abolish or reduce the ability of a protease to cleave wildtype and/or mutant Htt. For example, the Htt proteolysis inhibitor can block or reduce the enzymatic activity of the protease. As another example, the Htt proteolysis inhibitor can modulate the expression level of the protease gene, for example, by inhibiting or reducing the transcription of the protease gene. In addition, the Htt proteolysis inhibitors can reduce the level of protease protein available to cleave Htt, for example, by inhibiting or reducing the translation of the protease mRNA, or increase the degradation of the protease mRNA and/or protein.

In some embodiments, an Htt proteolysis inhibitor can act indirectly on Htt and/or the proteases that can cleave Htt. For example, the Htt proteolysis inhibitor can act to directly or indirectly activate a protein that inhibits the activation of one or more proteases that can cleave Htt, for example, by inhibiting or reducing the degradation of such protein, or by increasing the expression level of such protein. Non-limiting examples of such Htt proteolysis inhibitors include anti-IKKβ small hairpin RNA, anti-sense IKKβ RNA, IKKα and Bcl-xL. In some embodiments, the Htt proteolysis inhibitor can act to inhibit a protein that can directly or indirectly activate one or more proteases that can cleave Htt. A non-limiting example of such protein is IKKβ. In some embodiments, the Htt proteolysis inhibitor blocks any process in the pathway above Htt proteolysis that leads to Htt proteolysis. In some embodiments, the Htt proteolysis inhibitor activates (or stimulates) any process in the pathway above Htt proteolysis that blocks Htt proteolysis. An example of such a pathway is shown in FIG. 8A.

Htt proteolysis inhibitors can act on various molecules involved in the Htt proteolysis pathway, for example the signaling pathway triggering the cleavage of Htt and the proteases that cleave Htt. In some embodiments, an Htt proteolysis inhibitor can be an IKKβ inhibitor. In some embodiments, an Htt proteolysis inhibitor can be an IKKα activator. In some embodiments, an Htt proteolysis inhibitor can be a caspase inhibitor. In some embodiments, an Htt proteolysis inhibitor can be a Bcl-xL inducer.

The ability of a compound to inhibit or reduce Htt proteolysis can be measured using assays that are known in the art. For example and without limitation, the ability of an Htt proteolysis inhibitor to prevent or reduce Htt proteolysis can be identified through monitoring the cleaved Htt product(s) and/or by monitoring a cell's survival. As an example, cells treated with one or more Htt proteolysis inhibitors for a desired period of time can be harvested and separated into cytoplasmic and nuclear fractions. The cells can be treated by one or more DNA damage agents, such as etoposide and γ-radiation, after the treatment of the Htt proteolysis inhibitors. The cytoplasmic portion is analyzed by SD-PAGE and western-blotting with Htt-specific antibodies. Full-length Htt and cleaved Htt product(s) can be identified in western blot based on their gel mobility, which is an indication of a protein's molecular weight. As another example, cells, such as neurons, can be treated with one or more Htt proteolysis inhibitors for a desired period of time before being treated with one or more DNA damage agents. Because the cleavage of Htt is known to promote neurodegeneration, the extent of Htt proteolysis can be determined through monitoring the survival and/or death of the cells.

In some embodiments, a DNA damaging agent is applied to the cells prior to a candidate Htt proteolysis inhibitor is applied. In some embodiments, a DNA damaging agent is applied to the cells after to a candidate Htt proteolysis inhibitor is applied. In some embodiments, a DNA damaging agent is applied concurrently to the cells as the candidate Htt proteolysis inhibitor is applied.

In some embodiments, cells are protected from DNA damage by inhibiting DNA damage-induced Htt proteolysis by contacting the cells with at least one Htt proteolysis inhibitor. In other embodiments, HD is treated by administering one or more Htt proteolysis inhibitors to a patient having or expected to develop HD.

In some embodiments, Htt proteolysis inhibitors are provided directly to the patient, such as by injection. In other embodiments, nucleic acids encoding one or more HPI proteins are obtained and inserted into appropriate expression vectors. Cells that can be subject to DNA damage-induced Htt proteolysis can then be transfected with the expression vector, such that the protein is expressed in the cells. Methods for such genetic therapies are known in the art and can be adapted by the skilled artisan as necessary. This includes both gene therapy where a lasting effect is achieved by a single treatment and gene therapy where the increased expression is transient. Selective expression of one or more HPI proteins in appropriate cells can be achieved by using vectors with tissue specific or inducible promoters or by producing localized infection with replication defective viruses, or by any other method known in the art.

In some embodiments, DNA damage blockers can be used to reduce Htt proteolysis or can be used in an initial screening pool to then determine which provide the desired Htt proteolysis blocking activity. Such DNA damage blockers can include anti-oxidants.

IKKβ Inhibitors

As discussed above, the term "IKKβ inhibitor" is used herein in a broad sense and includes any molecule that partially or fully blocks, inhibits or neutralizes a biological activity mediated by IKKβ. In some embodiments it can prevent the activation of IKKβ. The term "IKKβ inhibitor" also includes any molecule that abolishes or reduces, the function or expression of IKKβ, or the efficiency of signaling through IKKβ.

The method by which IKKβ is inhibited is not limited in any way. In some embodiments, the IKKβ inhibitor can act directly on IKKβ, for example by binding to IKKβ, to prevent or reduce activation of IKKβ. In some embodiments, the IKKβ inhibitor can interfere, preferably abolish or reduce, IKKβ from interacting with a binding partner or a substrate, such as Bcl-xL and I-κB. In some embodiments, the IKKβ inhibitor can interfere, preferably abolish or reduce, the ability of IKKβ to phosphorylate a substrate, such as Bcl-xL and I-κB. In some embodiments, the IKKβ inhibitor can modulate the level of IKKβ gene expression, for example, inhibiting or reducing the transcription of IKKβ gene. In some embodiments, the IKKβ inhibitor can modulate the levels of IKKβ protein in cells by, for example, inhibiting or reducing the translation of IKKβ mRNA, or increasing the degradation of IKKβ mRNA or IKKβ protein. In some embodiments, the IKKβ inhibitor can interact with a molecule that is in an IKK dependent pathway, preferably downstream from IKKβ. In some embodiments, the IKKβ inhibitor can block the interaction of IKKβ with wildtype and/or mutant Htt.

The types of IKKβ inhibitor are not limited in any way. IKKβ inhibitors include, for example, small molecules, nucleic acids, antibodies, peptides, etc. In one embodiment, the IKKβ inhibitor can be a small molecule that binds to IKKβ, for example a Src tyrosine kinase inhibitor such as herbimycin. In some embodiments, the IKK inhibitor can be a compound that blocks interaction of IKKβ and it binding partner. A non-limiting example of such a compound is a NEMO (IKKγ) binding peptide (see, for example, Dai et al. J. Biol. Chem. 279(36):37219 (2004); Eijiro, J., et al. Nat. Med. 10(6):617 (2004); Siegmund, D., et al. J. Biol. Chem. 276: 43708 (2001); May, M. J., et al. Science 289:1550 (2000); and Li, Q., et al. Science 284:1999 (1999), each of which is incorporated by reference herein). NEMO binding peptides inhibit the activation of IKKβ by blocking the interaction of IKKγ with IKKβ and IKKα. An example of NEMO binding peptide is available from Calbiochem (Cat. No. 480025). In some embodiments, the IKK inhibitor is a compound that blocks IKKβ activation, for example, sodium salicylate. In some embodiments, the IKKβ inhibitor is a retinoid-related compound or a cyclopentenone prostaglandin. In some embodiments, the IKKβ inhibitor is a nucleic acid, for example, an anti-IKKβ small-hairpin RNA (shRNA) and IKKβ anti-sense RNA.

Antibodies that can block activation of IKKβ are also suitable for use in methods disclosed herein. Preferred antibodies bind to one or more subunits of the IKK complex. For example, an antibody can bind to IKKβ and prevent interaction between IKKβ and its binding partner (for example IKKγ and IKKα) and/or its substrate (for example Bcl-xL). In some embodiments, an antibody can also bind to one or more binding partner and/or substrate of IKKβ. In some embodiments, an antibody that prevents IKKβ from phosphorylating I-κB can be used. In some embodiments, an anti-IKK antibody prevents interaction of IKK and wildtype and/or mutant Htt can be used. The antibodies are not limited in any way, but are preferably monoclonal antibodies, more preferably human or humanized monoclonal antibodies. Antibodies to IKK can be prepared using methods that are well known in the art and inhibitory antibodies can be identified using the methods described herein.

Many other IKKβ inhibitors are also suitable to be used in the methods disclosed herein. For example, Yin et al. (Nature, 396:77-80, 1998) identified aspirin and salicylate as inhibitors of IKK; Kapahi et al. (J. Biol. Chem., 275(46):36062-36066, 2000) described that arsenite potently inhibited IKKβ activation by binding to Cys-179 in the activation loop of IKKβ; Ojo-Amaize et al. (Cell. Immunol., 209:149-157, 2001) identified hypoestoxide as an inhibitor of IKKβ; Burke et al. (J. Biol. Chem., 278(3):1450-1456, 2003) identified BMS-345541 (4(2'-aminoethyl)amino-1,8-dimethylimidazo (1,2-a)quinoxaline) as an IKKβ inhibitor. Various examples of IKKβ inhibitors are also disclosed in U.S. Pat. No. 7,279, 288, including dominant negative forms of IKK, such as DN-IKKγ; dominant negative forms of the E3-ubiquitin ligase βTrCP, such as ΔF-βTrCP; small molecule inhibitors such as herbimycin, sodium salicylate, retinoid-related compounds, cyclopentenone prostaglandins; NEMO binding peptides; and an antibody that inhibits IKKβ activity. In addition, Kempson et al. (J. Med. Chem., 52:1994-2005, 2009) described a number of examples of tricyclic inhibitors of IKKβ, including oxazole-based, thiazole-based, and imidazole-based IKKβ inhibitors. The contents of the references cited in this paragraph are expressly incorporated herein by reference in their entireties.

The ability of a molecule to inhibit IKKβ activation can be measured using assays that are well known in the art. For example and without limitation, IKKβ inhibitors can be identified using immune kinase assays and gene reporter assay. Briefly, in an immune kinase assay, immunoprecipitated IKKβ can be examined for the ability to phosphorylate GST-IκBα in vitro. For example, IKK complexes can be immunoprecipitated from cleared striatal extracts from animals or cells treated with the putative IKKβ inhibitor. The IKK complexes can then be depleted of IKKα and IKKγ by incubation with using IKKα and IKKγ antibodies coupled to protein G. The depleted lysates can be used to isolate IKKβ complexes with anti-IKKβ antibody. GST-IκBα can be used as a substrate to measure kinase activity in the presence of $^{32}$P-γ-ATP for 30 minutes at 30° C. Products are examined by SDS-PAGE followed by autoradiography. Gene reporter assays can be used to measure downstream effects of IKKβ, such as NF-κB activation. For example, a plasmid based reporter, pNF-κB-luciferase, with five enhancer elements and a control plasmid without NF-κB binding sites, pCIS-CK-luciferase, can be used to verify inhibition of NF-κB activity in cells treated with the putative inhibitor. The skilled artisan will be able to select the appropriate assays and reaction conditions based on the particular circumstances.

Additional examples of methods for identifying and characterizing IKKβ inhibitors are described in U.S. Pat. No. 6,649,654 and U.S. Publication No. 20030232888, the contents of which are incorporated herein by reference in their entireties.

IKKα Activators

As discussed above, "IKKα activator" is used herein in a broad sense and includes any molecule that partially or fully activates a biological activity mediated by IKKα. The term "IKKα activator" also includes any molecule that mimics a biological activity mediated by IKKα and specifically changes, preferably increases, the function or expression of IKKα, or the efficiency of signaling through IKKα.

The method by which the biological activity mediated by IKKα is activated is not limited in any way. In some embodiments, an IKKα activator can be a constitutively active mutant of IKKα, thereby the IKKα mutant can interfere, preferably abolish or reduce, activation of IKKβ. In some embodiments, an IKKα activator can act directly on IKKα, for example by binding to IKKα, to increase the activation of IKKα. In some embodiments, an IKKα activator can enhance the ability of IKKα to interact with a binding partner or a substrate. In some embodiments, an IKKα activator can modulate the level of IKKα gene expression, preferably increasing the level of transcription of IKKα gene. In some embodiments, an IKKα activator can modulate the levels of IKKα protein in cells by, for example, increasing the translation of IKKα mRNA, or decreasing the degradation of IKKα mRNA or IKKα protein. In some embodiments, an IKKα activator can interact with a molecule that is in an IKK dependent pathway, preferably downstream from IKKα.

The types of IKKα activator are not limited in any way. Preferred IKKα activators include, for example, small molecules, nucleic acids, antibodies, peptides, etc. In some embodiments, the IKKα activator can be insulin-like growth factors (IGFs) such as IGF-1 and IGF-2. In some embodiments, the IKKα activator can be netrin.

The ability of a molecule to increase IKKα activation can be measured using assays that are well known in the art. For example and without limitation, IKKα activators can be identified using immune kinase assays and gene reporter assay. In an example of immune kinase assays, MESC2.10 neurons engineered to express a Flag-tagged IKKα are starved for growth factors for 8 hours. Candidate IKKα activators are added, respectively, to the starved MESC2.10 neurons for desired period of time. Neurons are harvested and cytoplasmic extracts are used to immunoprecipitate IKKα using agarose beads coupled to anti-Flag antibody. Complexes are assayed for the ability to phosphorylate a recombinant substrate GST-IκBα in the presence of radioactive $\gamma$-$^{32}$P. Products are examined by SDS-PAGE followed by autoradiography. The density of the bands in the western blot can be used to determine whether the candidate IKKα activator activates IKKα.

Of course, as provided herein, IKKα activators and IKK beta inhibitors can be assayed by looking for the appropriate reduction in Htt proteolysis.

Caspase Inhibitors

As discussed above, the term "caspase inhibitor" is used in a broad sense and includes any molecule that partially or fully blocks, inhibits or neutralizes a biological activity mediated by one or more caspases, preferably by preventing or reducing the activation of the caspase(s) or the proteolytic activity of the caspase(s). The term "caspase inhibitor" also includes any molecule that abolishes or reduces, the function or expression of one or more caspases, or the efficiency of caspase cleavage.

The method by which caspases are inhibited is not limited in any way. In some embodiments, a caspase inhibitor can act directly on one or more procaspases, for example by binding to procaspase-3 or procaspase-6, to prevent or reduce activation of procaspases. In some embodiments, a caspase inhibitor can interfere, preferably abolish or reduce, one or more caspase, for example caspase-3 and caspase-6, from interacting with a substrate, such as wild type and/or mutant Htt. In some embodiments, a caspase inhibitor can interfere, preferably abolish or reduce, the ability of one or more caspases to cleave a substrate, such as wild type and/or mutant Htt. In some embodiments, a caspase inhibitor can modulate the expression level of one or more caspase genes, for example, inhibiting or reducing the transcription of caspase-3 and/or caspase-6 genes. In some embodiments, a caspase inhibitor can modulate the levels of one or more caspases in cells by, for example, inhibiting or reducing the translation of caspase mRNA, or increasing the degradation of caspase mRNA or caspase protein. In some embodiments, a caspase inhibitor can interact with a molecule that is upstream from caspase in the Htt proteoylysis pathway, for example, Bcl-xL, IKKβ, and IKKα. In some embodiments, a caspase inhibitor can interact with a molecule that is downstream from caspase in the Htt proteolysis pathway. In some embodiments, a caspase inhibitor can prevent or reduce the activation of caspases through increasing the activity or protein level of Bcl-xL.

The types of caspase inhibitor are not limited in any way. Caspase inhibitors include, for example, small molecules, nucleic acids, antibodies, peptides, etc. In some embodiments, the caspase inhibitor can be a broad-spectrum caspase inhibitor. Examples of broad-spectrum caspase inhibitor include, but are not limited to, caspase inhibitors BOC-D-FMK, Z-VAD-FMK and Q-VD-OPH. In some embodiments, the caspase inhibitor can be caspase-3/7 inhibitor Z-DEVD-FMK. In some embodiments, the caspase inhibitor can be caspase-3 inhibitor Ac-DEVD-CHO. In some embodiments, the caspase inhibitor can be caspase-6 inhibitor Ac-VEID-CHO. In some embodiments, the caspase inhibitor can be caspase-9 inhibitor Z-LEHD-FMK.

Antibodies that can block activation of one or more caspases are also suitable for use in methods disclosed herein. Preferred antibodies bind to one or more caspases. For example, an antibody can bind to caspase-3 and/or caspase-6 and prevent interaction between caspase-3 and/or caspase-6 and the substrate (such as wildtype and/or mutant Htt). The antibodies are not limited in any way, but are preferably monoclonal antibodies, more preferably human or humanized monoclonal antibodies. Antibodies to one or more caspases can be prepared using methods that are well known in the art and inhibitory antibodies can be identified using the methods described herein.

The ability of a molecule to inhibit caspase activation can be measured using assays that are well known in the art. For example and without limitation, caspase inhibitors can be identified using colorimetric assay. For example, in the case of determining whether a candidate compound is a caspase-3 inhibitor, cells can be pre-incubated with the candidate caspase inhibitor before being lysed. The cell lysate is then incubated with a caspase-3 substrate, for example DEVD conjugated to p-nitroanaline) in a 96-well plate at 37° C. for 1 hour. Enzyme activity for caspase-3 is measured with a microplate reader at 405 nm. The skilled artisan will be able to select the appropriate assays and reaction conditions based on the particular circumstances.

Of course, as provided herein, caspase inhibitors can be assayed by looking for the appropriate reduction in Htt proteolysis.

Bcl-xL Inducer

As used herein, the term "Bcl-xL inducer" is used in the broadest sense and includes any molecule that partially or fully activates a biological activity mediated by Bcl-xl. The term "Bcl-xL inducer" also includes any molecule that mimics a biological activity mediated by Bcl-xl and specifically changes, preferably increases, the function or expression of Bcl-xl. In some embodiments, Bcl-xL inducers can also prevent or reduce the phosphorylation of Bcl-xl, or the degradation of Bcl-xL.

The method by which the biological activity mediated by Bcl-xl is activated is not limited in any way. In some embodiments, the Bcl-xL inducer can be a mutant Bcl-xl that is resistant to phosphorylation. For example, the mutant Bcl-xl may not be phosphorylated by a kinase (such as IKKβ) or the mutant Bcl-xl may only be phosphorylated by a kinase (such as IKKβ) in a reduced rate compared with wildtype Bcl-xL. In some embodiments, the Bcl-xL inducer can be a mutant Bcl-xl that has a lower turnover rate than the wildtype Bcl-xl. For example, a mutant Bcl-xl may take a longer time to be degraded than the wildtype Bcl-xl. In some embodiments, the Bcl-xL inducer can modulate, preferably abolish or reduce, the activation of one or more caspases. In some embodiments, the Bcl-xL inducer can act directly on Bcl-xl, for example by binding to Bcl-xl, to prevent or reduce the phosphorylation of Bcl-xl. In some embodiments, the Bcl-xL inducer can inhibit or reduce the ability of a kinase that target Bcl-xl to interact with a substrate, for example, by binding and/or sequestering the kinase. In some embodiments, the Bcl-xL inducer can modulate the level of Bcl-xl gene expression, preferably increasing the level of transcription of Bcl-xl gene. In some embodiments, the Bcl-xL inducer can modulate the levels of Bcl-xl protein in cells by, for example, increasing the translation of Bcl-xl mRNA, or decreasing the degradation of Bcl-xl mRNA or Bcl-xl protein. In some embodiments, the Bcl-xL inducer can interact with a molecule that is upstream from Bcl-xl in the Htt proteolysis pathway, such as IKKβ and IKKα. In some embodiments, the Bcl-xL inducer can interact with a molecule that is downstream from Bcl-xl in the Htt proteolysis pathway.

The types of Bcl-xL inducer are not limited in any way. Preferred Bcl-xL inducers include, for example, small molecules, nucleic acids, antibodies, peptides, etc. In some embodiments, the Bcl-xL inducer can be IKKα. In other embodiments, the Bcl-xL inducer can be green tea polyphenol (GTP) or epigallocatechin gallate (EGCG). In still other embodiments, the Bcl-xL inducer can be Bcl-xL. In yet other embodiments, the Bcl-xL inducer can be IGFs, including, but not limited to, IGF-1 and IGF-2. In some embodiments, the Bcl-xL inducer is BDNF. In some embodiments, the Bcl-xL inducer is cystamine or memantine.

The ability of a molecule to increase Bcl-xL activation (or result in Bcl-xL induction) can be measured using assays that are well known in the art. For example and without limitation, Bcl-xL inducers can be identified through examining the amount of intact Bcl-xL and/or phosphorylated Bcl-xL in western blot assay. For example, cells can be treated with a candidate Bcl-xL inducer before being exposed to a DNA damage-inducing agent, such as etoposide. Cells are harvested and cytoplasmic extracts are examined by SDS-PAGE followed by Bcl-xl-specific antibody probing and autoradiography. The density of the Bcl-xL protein bands in the western blot can be used to determine whether the candidate Bcl-xL inducer activates Bcl-xl or not.

Of course, as provided herein, Bcl-xL inducers can be assayed by looking for the appropriate reduction in Htt proteolysis.

Any of the herein described Htt proteolysis inhibitors (e.g., Bcl-xL inducers, IKKα activators, IKKβ inhibitor, caspase inhibitors, etc.) can be assayed by looking at any step further down in the cascade (see, for example FIG. 8A). Thus, any of the assays can also look at any of the subsequent steps, though and including Htt proteolysis and cell death, symptoms of the disorder, etc). Furthermore, as will be appreciated by one of skill in the art, a molecule can fall into more than one category. For example, an IKK beta inhibitor can result in less Bcl-xL induction (meaning that it will also qualify as a Bcl-xL inducer), which can in turn result in less caspase 3 activity (meaning it would also qualify as a caspase 3 inhibitor). Thus, unless explicitly identified as such, these terms are not mutually exclusive.

Compositions Comprising Htt Proteolysis Inhibitors

In some embodiments, a method of treatment involving administration of an effective amount of a composition comprising one or more Htt proteolysis inhibitors is provided. In some embodiments, the composition comprises at least one Htt proteolysis inhibitor that is a small molecule or peptide, for example an IKKβ inhibitor selected from herbimycin, NF-κB essential modulator (NEMO) binding peptide, sodium salicylate, retinoid-related compounds, cyclopentenone prostaglandins, IKKα, BMS-345541 (4(2'-aminoethyl) amino-1,8-dimethylimidazo(1,2-a)quinoxaline), tricyclic based inhibitors of IKK, and some combination thereof; an IKKα activator selected from IGF-1, netrin, and some combination thereof; a Bcl-xL inducer selected from green tea polyphenols (GTP), epigallocatechin-3-gallate (EGCG), IKKα, Bcl-xL, IGF, BDNF, cystamine, memantine, and some combination thereof; and a caspase inhibitor selected from broad-spectrum caspase inhibitors BOC-D-FMK, Z-VAD-FMK and Q-VD-OPH; caspase-3/7 inhibitor Z-DEVD-FMK; caspase-3 inhibitor Ac-DEVD-CHO; caspase-6 inhibitor Ac-VEID-CHO; caspase-9 inhibitor Z-LEHD-FMK; and some combination thereof. In other embodiments, the composition comprises an Htt proteolysis inhibitor that is an antibody or other polypeptide, such as a human or humanized anti-IKKβ monoclonal antibody. In still other embodiments, the composition comprises an Htt proteolysis inhibitor that is a nucleic acid, for example, an anti-IKKβ small-hairpin RNA (shRNA) and IKKβ anti-sense RNA. In some embodiments, the HPI is included in an amount suitable for the treatment of a DNA damage induced neurodegeneration disorder. In some embodiments, the HPI is combined with other ingredients that are suitable for the treatment of a DNA damage induced neurodegeneration disorder, such as HD.

In pharmaceutical dosage forms, the Htt proteolysis inhibitors can be used alone or in appropriate association, as well as in combination with other pharmaceutically active or inactive compounds. The Htt proteolysis inhibitors can be formulated into pharmaceutical compositions containing a single Htt proteolysis inhibitor or a combination of two or more Htt proteolysis inhibitors. For example, a pharmaceutical composition can contain two or more different Htt proteolysis inhibitors. In some embodiments, the pharmaceutical composition contains two or more different Htt proteolysis inhibitors having the same mode of action. For example, a pharmaceutical composition can contain two Htt proteolysis inhibitors where both Htt proteolysis inhibitors are IKKβ inhibitors that block IKKβ from phosphorylating Bcl-xL. As another example, a pharmaceutical composition can contain two Htt proteolysis inhibitors where one of the Htt proteolysis inhibitors is an IKKβ inhibitor that inhibits IKKβ from phosphorylating Bcl-xL and the other Htt proteolysis inhibitor is an IKKβ inhibitor that inhibits the transcription of IKKβ gene. In another embodiment, the pharmaceutical composition can contain two or more Htt proteolysis inhibitors having different methods of action. For example, one Htt proteolysis inhibitor can be an IKKβ inhibitor that blocks IKKβ from phosphorylating Bcl-xL, while a different Htt proteolysis inhibitor can be an IKKα activator that increases the gene expression of IKKα.

In some embodiments, where more than one type of HPI is included that works at a different point in the flow path depicted in FIG. 8A, the amount of each HPI used need not be individually sufficient to stop the signal cascade by any single HPI; however, the combination of the HPIs, each acting at a different level can be sufficient to achieve the desired result and thus be effective. Such a combination allows for some residual activity to remain in those levels that are to be inhibited and/or avoiding over stimulation at those levels that are to be activated.

The Htt proteolysis inhibitors can be formulated into pharmaceutical compositions by combination with appropriate, pharmaceutically acceptable carriers or diluents (Remington, The Science and Practice of Pharmacy, 19.sup.th Edition, Alfonso, R., ed., Mack Publishing Co., Easton, Pa. (1995), and can be formulated into preparations in solid, semi-solid, liquid or gaseous forms, such as tablets, capsules, powders, granules, ointments, solutions, suppositories, injections, inhalants and aerosols depending on the particular circumstances.

The pharmaceutically acceptable excipients, such as vehicles, adjuvants, carriers or diluents, are readily available. Moreover, pharmaceutically acceptable auxiliary substances, such as pH adjusting and buffering agents, antioxidants, low molecular weight (less than about 10 residues) polypeptides, tonicity adjusting agents, stabilizers, wetting agents and the like, are readily available. "Carriers" when used herein refers to pharmaceutically acceptable carriers, excipients or stabilizers which are nontoxic to the cell or mammal being exposed to the carrier at the dosages and concentrations used.

A Htt proteolysis inhibitor to be used for in vivo administration is preferably sterile. The sterility can be accomplished by any method known in the art, such as by filtration using sterile filtration membranes, prior to or following lyophilization and reconstitution. In some embodiments the Htt proteolysis inhibitors are available commercially in sterile form.

The compositions containing one or more Htt proteolysis inhibitors can be placed into a container with a sterile access port, for example, an intravenous solution bag or vial having a stopper pierceable by a hypodermic injection needle.

The Htt proteolysis inhibitors can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The Htt proteolysis inhibitors can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the active ingredient can be in powder form for constitution with a suitable vehicle, for example, sterile pyrogen-free water, before use. The compounds can also be formulated in rectal compositions such as suppositories or retention enemas, for example, containing conventional suppository bases such as cocoa butter or other glycerides.

In addition to the formulations described above, the Htt proteolysis inhibitors can also be formulated as a depot preparation. Such long-acting formulations can be administered by implantation (for example, subcutaneously or intramuscularly) or by intramuscular injection. Thus, for example, the Htt proteolysis inhibitors can be formulated with suitable polymeric or hydrophobic materials (for example as an emulsion in an acceptable oil) or ion exchange resins, or as sparingly soluble derivatives, for example, as a sparingly soluble salt.

For oral preparations, the Htt proteolysis inhibitors can be combined with appropriate additives to make tablets, powders, granules or capsules. For example, the Htt proteolysis inhibitors can be combined with conventional additives such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Liquid preparations for oral administration can take the form of, for example, solutions, syrups or suspensions, or they can be presented as a dry product for constitution with water or other suitable vehicle before use. Preparations for oral administration can be suitably formulated to give controlled release of the active compound.

Htt proteolysis inhibitors can also be aerosolized or otherwise prepared for administration by inhalation. For example a fluorocarbon formulation and a metered dose inhaler, or inhaled as a lyophilized and milled powder. For administration by inhalation, the Htt proteolysis inhibitors can be utilized in aerosol formulation to be administered via inhalation. The Htt proteolysis inhibitors can also be formulated into pressurized acceptable propellants such as dichlorodifluoromethane, propane, nitrogen and the like.

If an Htt proteolysis inhibitor is coadministered with another Htt proteolysis inhibitor, or with another agent having similar biological activity, the different active ingredients can be formulated together in an appropriate carrier vehicle to form a pharmaceutical composition. Alternatively, Htt proteolysis inhibitors can be formulated separately and administered simultaneously or in sequence.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In some embodiments, the HPI is formulated for cellular use, and need not be formulated for administration to a subject. In some embodiments, the HPI is formulated for direct application into the brain, e.g., direct injection or pump based delivery systems and methods. In some embodiments, the HPI is formulated for or applied via intraventricular application.

Methods of Treatment

In some embodiments, a method of treating (including preventing, (meaning reducing the risk of or time of onset of) an individual suffering from or at risk of HD is provided, where the method comprises administering to the individual one or more HPIs. In some embodiments, this involves administering a composition comprising one or more Htt proteolysis inhibitors at a therapeutically effective dose. As discussed above, treatment can include an amelioration of the symptoms associated with the pathological condition afflicting the host, where amelioration is used in a broad sense to refer to at least a reduction in the magnitude of a parameter, e.g., symptom, associated with the pathological condition being treated, such as neuronal cell death. As such, treatment includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition. However, treatment can also be delay or slowing of disease progression, amelioration or palliation of the disease state, and remission (whether partial or total), whether detectable or undetectable. In some embodiments, treatment includes the detectable decrease in the level of cleaved Htt in a cell, host, or sample from a host.

A variety of individuals are treatable. Generally, such individuals are mammals, where the term is used broadly to describe organisms which are within the class mammalia, including the orders carnivore (for example, dogs and cats), rodentia (for example, mice, guinea pigs and rats), and primates (for example, humans, chimpanzees and monkeys). In preferred embodiments, the individuals are humans.

The Htt proteolysis inhibitors can be administered using any convenient protocol capable of resulting in the desired therapeutic activity. A specific protocol can readily be determined by a skilled practitioner without undue experimentation based on the particular circumstances. Thus, the Htt proteolysis inhibitors can be incorporated into a variety of formulations for therapeutic administration, as discussed above, depending on the protocol adapted by the supervising clinician.

Each dosage for human and animal subjects preferably contains a predetermined quantity of one or more Htt proteolysis inhibitors calculated in an amount sufficient to produce the desired effect, in association with a pharmaceutically acceptable diluent, carrier or vehicle. Again, the actual dosage forms will depend on the particular compound employed, the effect to be achieved, and the pharmacodynamics associated with each compound in the host.

Administration of the Htt proteolysis inhibitors can be achieved in various ways, including intracranial, for example injection directly into the brain tissue or into the cerebrospinal fluid, oral, buccal, rectal, parenteral, intraperitoneal, intradermal, transdermal, intracheal, intracerebral, etc., administration. The Htt proteolysis inhibitors can be administered alone or in combination with one or more additional therapeutic agents. Administration "in combination with" one or more further therapeutic agents includes both simultaneous (at the same time) and consecutive administration in any order.

Administration can be chronic or intermittent, as deemed appropriate by the supervising practitioner, particularly in view of any change in the disease state or any undesirable side effects. "Chronic" administration refers to administration of one or more Htt proteolysis inhibitors in a continuous manner while "intermittent" administration refers to treatment that is not done without interruption.

Combinations of Htt proteolysis inhibitors for simultaneous administration are used in some embodiments. For example, two or more different Htt proteolysis inhibitors can be administered in combination.

In some embodiments, one or more Htt proteolysis inhibitors are administered by intracranial injection. The injection will typically be directly into affected brain regions or into the cerebrospinal fluid.

An effective amount of an Htt proteolysis inhibitor to be employed therapeutically will depend, for example, upon the therapeutic objectives, the route of administration, the nature of the Htt proteolysis inhibitor, and the condition of the patient. Accordingly, it can be useful for the therapist to titer the dosage and modify the route of administration as required to obtain the optimal therapeutic effect. A typical daily dosage can range from about 0.01 µg/kg to up to about 1 mg/kg or more, depending on the factors mentioned above. Preferably, a typical daily dosage ranges from about 1 µg/kg to about 100 µg/kg. Typically, the clinician will administer an Htt proteolysis inhibitor until a dosage is reached that provides the best clinical outcome. The progress of this therapy is easily monitored by conventional assays.

Toxicity and therapeutic efficacy of a Htt proteolysis inhibitor can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. The Htt proteolysis inhibitors exhibiting large therapeutic indices are preferred. While compounds that exhibit toxic side effects can be used, care can be taken to design a delivery system that targets such compounds to the site of affected tissue in order to minimize undesired side effects.

In some embodiments, the HPI can be used for neuroprotection for disorders that relate to DNA damage induce neurodegeneration. In some embodiments, the HPI can be used to reduce one or more aging effects that relates to DNA damage induce neurodegeneration. In some embodiments, the neuroprotection and/or aging effects are independent of any disease and provide a benefit in light of their ability to reduce the role of DNA damage in neurodegeneration. In some embodiments, the neuroprotection and/or aging effects exhibit elevated levels of cleaved Htt (mutant and/or wild type).

Screening Assays for Htt Proteolysis Inhibitors

In some embodiments, compounds useful in protecting cells from DNA damage are identified by screening for compounds that inhibit Htt proteolysis. In some embodiments, compounds useful for reducing/blocking Htt proteolysis from DNA damage are identified by screening for compounds that inhibit Htt proteolysis when the tested sample is also exposed to a DNA damaging agent. In some embodiments, DNA damage reducing agents can be screened to determine which ones are useful for Htt proteolysis inhibitors. Screening assays are well known in the art and can readily be adapted to identify any of the above screens.

The compounds which can be screened in accordance with the present application include, but are not limited to, small molecules, nucleic acids, peptides, antibodies and fragments thereof, and other organic compounds (e.g., peptidomimetics). The compounds can include, but are not limited to, soluble peptides, including members of random peptide libraries (see e.g., Lam, K. S. et al., 1991, Nature 354:82-84; Houghten, R. et al., 1991, Nature 354:84-86), and combinatorial chemistry-derived molecular libraries made of D- and/or L-configuration amino acids, phosphopeptides (including, but not limited to members of random or partially degenerate, directed phosphopeptide libraries; see e.g., Songyang, Z. et al., 1993, Cell 72:767-778), antibodies (including, but not limited to, polyclonal, monoclonal, humanized, anti-idiotypic, chimeric or single chain antibodies, and FAb, F(abN)$_2$ and FAb expression library fragments, and epitope-binding fragments thereof), and small organic or inorganic molecules, including libraries thereof. Other compounds that can be screened in accordance with the present application include, but are not limited to, small organic molecules, for example, those which are able to cross the blood-brain barrier.

Libraries of known compounds, including natural products or synthetic chemicals, and biologically active materials, including proteins, can be screened for compounds which are inhibitors of Htt proteolysis.

As discussed herein, IKKβ, caspases such as caspase-3 and caspase-6, IKKα, and Bcl-xL are involved in the Htt proteolysis pathway (FIG. 8A). Examples of Htt proteolysis inhibitors include, but are not limited to, IKKβ inhibitors, caspase inhibitors, IKKα activators, and Bcl-xL inducers. Htt proteolysis inhibitors can include, but are not limited to, compounds that interact with (for example, bind to) one or more HP proteins, such as IKKβ, a caspase, IKKα, and Bcl-xL; compounds that interfere with the interaction of one or more HP proteins with its binding partners, cognate or substrate; compounds that modulate gene expression of one or more HP gene, such as compounds that modulate the level of IKKα gene expression; and compounds that modulate the levels of one or more HP proteins in the cell. Assays can additionally be utilized which identify compounds that bind to regulatory sequences of one or more HP gene (e.g., promoter sequences) and, consequently, may modulate gene expression of the HP gene(s). See Platt, K. A., 1994, J. Biol. Chem. 269:28558-28562, which is incorporated herein by reference in its entirety.

The two-hybrid system, a method for detecting protein interactions in vivo, can also be used to identify Htt proteolysis inhibitors, including, but not limited to, IKKβ inhibitors, caspase inhibitors, IKKα activators, and Bcl-xL inducers. One example of the two-hybrid system has been described (Chien et al., 1991, Proc. Natl. Acad. Sci. USA, 88:9578-9582, herein incorporated by reference) and is commercially available from Clontech (Palo Alto, Calif.). For example, the two-hybrid system may be adapted for screening for and identify small molecule HPI that, for example, can disrupt the interaction of one HP protein and its substrates and/or binding partners.

Briefly, in the two-hybrid system, plasmids can be constructed to encode two hybrid proteins: one plasmid can include nucleotides encoding the DNA-binding domain of a transcription activator protein fused to a nucleotide sequence encoding a HP protein, and a second plasmid can include nucleotides encoding the activation domain of the transcription activator protein fused to a cDNA encoding an unknown protein which has been recombined into this plasmid as part of a cDNA library. The DNA-binding domain fusion plasmid and the cDNA library are transformed into a strain of *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

By way of example, and not by way of limitation, an IKKβ yeast reporter strain can be generated by cotransforming a plasmid encoding IKKβ gene fused to a DNA-activation domain and a plasmid encoding a hybrid of an IKKγ gene product fused to the DNA-binding domain into a yeast reporter strain. The resulting IKK yeast reporter strain is useful for screening libraries, such as small molecule libraries, for IKKβ inhibitors. Small molecules capable of disrupting the interaction between IKKβ and IKKγ inhibit expression of the lacZ reporter.

The two-hybrid system or related methodology may also be used to screen activation domain libraries for proteins that interact with the "bait" gene product. By way of example, and not by way of limitation, IKKα can be used as the bait gene product. Total genomic or cDNA sequences are fused to the DNA encoding an activation domain. This library and a plasmid encoding a hybrid of a bait IKKα gene product fused to the DNA-binding domain are cotransformed into a yeast reporter strain, and the resulting transformants are screened for those that express the reporter gene. The positive clones that display positive interaction are identified and the library plasmids responsible for reporter gene expression are isolated. DNA sequencing is then used to identify the proteins encoded by the library plasmids. Proteins identified in the two-hybrid system can then be tested for its ability to interact with the bait IKKα.

Small molecules can also have the ability to act as inhibitors or activators of a HP protein and thus may be screened for such activity. Small molecules preferably have a molecular weight of less than 10 kD, more preferably less than 5 kD and even more preferably less than 2 kD. Such small molecules may include naturally-occurring small molecules, synthetic organic or inorganic compounds, peptides and peptide mimetics. However, small molecules in the present application are not limited to these forms. Extensive libraries of small molecules are commercially available and a wide variety of assays are well known in the art to screen these molecules for the desired activity.

In some embodiments, the screening assay includes a cell that contains the appropriate cascade components (e.g., some part of what is shown in FIG. 8A). The cell (or cell culture) can then be tested under conditions that would otherwise lead to Htt proteolysis, in combination with candidate HPIs. In some embodiments, numerous test compounds are tested in a pool (for example more than one, such as 2, 5, 10, 20, 50, 100 or more test compounds) to determine if their presence or absence alters the resulting cleaved Htt protein. In some embodiments, the final Htt protein is assayed for degree of processing (e.g., percent cleaved vs. uncleaved or absolute amount of cleaved protein). In some embodiments, any intermediate along the pathway is assayed to see if the particular increase or decrease is detected. In some embodiments the result is reviewed in terms of cell health or survival or organism health or survival. In some embodiments, the screening assay includes a step for inducing DNA damage in the cell or host. Thus, in some embodiments, a kit for performing a screening assay can include a cleaved Htt protein and subsequent neuronal death detection component and a DNA damaging component.

In some embodiments, the candidate Htt proteolysis inhibitor can be a known IKKβ inhibitor, a known caspase inhibitor, a known IKKα activator, and/or a known Bcl-xL inducer. Thus, in some embodiments, one starts with such a compound and then further checks to determine that it has the desired level of effectiveness on DNA damage induced Htt proteolysis, at the desired concentration, with acceptable (if any) side-effects.

In some embodiments, a kit for screening for IKKα activators, Bcl-xL inducers, caspase inhibitors, and/or IKK beta inhibitors is provided. In some embodiments, the kit comprises a control IKKα activator (or appropriate molecule) and a means for monitoring DNA damage-induced Htt proteolysis. As disclosed herein, a means for monitoring DNA damage-induced Htt proteolysis includes, but is not limited to, testing the cleavage of Htt by monitoring a cell's survival and/or death, or through monitoring the full-length Htt and/or the cleaved Htt product(s). In some embodiments, the cleavage of Htt is tested by monitoring a cell's survival and/or death. For example, the cell's survival and/or death can be directly detected using trypan blue, where trypan blue can only traverses the membrane in a dead cell, but not a viable cell. In other embodiments, the cleavage of Htt can be tested by monitoring the amount of the full-length Htt and/or the cleaved Htt product(s). For example, the amount of the full-length Htt and/or the cleaved Htt product(s) can be detected using western blot.

EXAMPLES

The following examples, including the experiments conducted and results achieved are provided for illustrative purposes only and are not to be construed as limiting upon the present application.

Experimental Methods

The following experimental methods were used, as appropriate, for Examples 1-5 described below.
Antibodies and Reagents.
Anti-Htt (mAb 2166), an PSD-95 antibodies were purchased from Millipore (Temecula, Calif.). Antibodies recognizing IKKγ, IKKβ, caspase-3, caspase 6 and p52/p100 were purchased from Cell Signaling Technolog (Danvers, Mass.). Anti-IKKα was purchased from BD Biosciences (San Diego, Calif.). Anti-Bcl-xL and anti-p53 antibodies were from Santa Cruz Biotechnologies (Santa Cruz, Calif.). Anti-Tuj-1 antibody was purchased from Covance (Berkeley, Calif.). Cell fractionation and EC detection kits including HRP-conjugated secondary antibodies were from PIERCE Biotechnology (Rockford, Ill.). Anti-γ-H2AX antibody, caspase-3 and caspase-6 activity kits, and recombinant Bcl-xL protein were obtained from R&D systems (Minneapolis, Minn.). Anti-laminB1 antibody DMEM/F12, N-2 and B-27 media supplements were purchased from Invitrogen (Carlsbad, Calif.). Fibroblast-growth factor-2 (FGF-2) was obtained from Promega (Madison, Wis.). Sodium salicylate, etoposide, and caspase-3 and caspase-6 inhibitors (Ac-DEVD-CHO and Ac-VEID-CHO, respectively), and anti-tubulin antibody were purchased from Sigma/Aldrich (St. Luis, Mo.). Recombinant active IKKα and IKKβ were purchased from Upstate Biotechnologies Lake Placid, N.Y.). Consensus NF-κB oligonucleotides for p65 and p52 coated onto 96 well and the corresponding antibodies for binding detection (TransFactor NF-κB p65 and p52) were purchased from Clontech (Mountain View, Calif.)

Plasmids.

WT IKKα was obtained from Tularik, Inc (San Francisco, Calif.). The lentiviral backbone (FUGW) and plasmids encoding the structural genes for viral production were obtained from David Baltimore at the California Institute of Technology.

Generation of MESC2.10 Human Neurons

MESC2.10 human neuroblasts were generated as described in Lotharius et al. (2002) J. Biol. Chem. 277: 38884-38894. Neuroblasts obtained from an 8 week-old human embryo were transduced with a retrovirus encoding a tetracycline-regulated v-myc to promote proliferation. These neuroblasts were grown on poly-lysine and laminin coated plates in DMEM/F12 in the presence N2 and B-27 neuronal supplements and 20 ng/ml FGF-2. To differentiate MESC2.10 cells, proliferation medium was replaced DMEM/F12 medium containing 2 μg/ml of doxycycline and 5 μM cAMP.

Mouse striatal neuronal precursors, $Hdh^{Q111/Q111}$, obtained from homozygous knock-in mice were propagated as described in Gines et al. (2003) J. Biol. Chem. 278: 50514-50522. Differentiation was carried out in DMEM/F12 medium containing N2 and B-27 supplements as described for MESC2.10 neurons.

Etoposide Treatment, Cell Fractionation and Western Blotting

MESC2.10 cells, differentiated for 9 days, were treated with 10 μM etoposide for the periods indicated in each figure. Neurons were harvested and separated into cytoplasmic and nuclear fractions using the NE-PER kit (PIERCE) according to instructions. For most experiments, ~120 μg of lysate were used for SDS-PAGE and Western blotting with the indicated antibodies. Reactive bands in Western blots were detected by enhanced chemiluminescence (ECL) using a gel documentation system. Sodium salicylate (5 mg/ml), caspase-3 inhibitor (Ac-DEVD-CHO) and caspase-6 inhibitor (Ac-VEID-CHO) were added at 20 μM 1 hr prior to etoposide treatment. To examine the effects of etoposide on mutant Htt, differentiated mouse striatal cells (HdhQ111/Q111) were treated with etoposide and analyzed as described for MESC2.10 cells.

Immunochemistry

Differentiated neurons on coverslips were treated with 10 μM etoposide for 4 hr. Cells were fixed and stained with a rabbit antibody that specifically recognizes H2aX phosphorylated at Ser 139 (γ-H2aX) (1:500). Anti-Tuj-1 was used to label the cytoplasm (1:1000). Goat anti-rabbit conjugated to FITC (green) and goat anti-mouse conjugated to rhodamine (red) was used as secondary antibodies. Pictures were captured with a confocal microscope.

Lentivirus Production

IKKα was cloned into the lentiviral FUGW vector under the control of a ubiquitin promoter. An EGFP-lentivirus was used as a control. The Bcl-xL cDNA was cloned from MESC2.10 neurons by RT-PCR using standard procedures and its identity confirmed by sequencing. The cDNA was subsequently inserted into FUGW lentiviral vector. The shRNAs for IKKβ were cloned in a lentiviral backbone. Lentiviruses were produced by transfection of 293 cells using calcium phosphate precipitation. Supernatants of virus-producing cells were harvested 48 hr post-transfection and concentrated on Amicon Ultra columns. An EGFP virus was used as a control to monitor viral titer. A multiplicity of infection of 4:1 was used to infect MESC2.10 neuroblasts. Expression of IKKα, Bcl-xL and reduction of IKKβ were determined by Western blotting.

Kinase Assay

IKKβ activity was assayed as described in Khoshnan (2004) J. Neurosci. 24: 7999-8008. To determine IKKα activity, lyastes were first depleted of IKKβ complexes using 4 μg of anti-IKKγ and anti-IKKβ antibodies coupled to protein G. The depleted lysates were used to isolate IKKα complexes with 2 μg of anti-IKKα antibody. GST-IκBα was used as a substrate to measure kinase activity. To examine whether IKKs phosphorylate Bcl-xL, 0.5 μg of either IKKα or IKKβ were incubated with 1 μg of full-length Bcl-xL in the presence of 32P-γ-ATP for 30 min at 30° C. GST protein was used as a negative control. All kinase products were examined by SDS-PAGE and autoradiography.

Assay of NF-κB Binding to Consensus DNA Oligonucleotides

Nuclear extracts for control or etoposide-treated MESC2.10 neurons were obtained using the cell fractionation kit from pierce according to the instructions provided. Fifty μg of each nuclear extract was incubated for an hour at room temperature on 96 well plates coated with consensus NF-κB oligonucleotides (p65 or p52). Mutated NF-κB oligonucleotides were used to confirm binding specificity. For competition assays, nuclear extracts were pre-incubated with NF-κB oligonucleotides for 1 hour on ice and then added to the coated wells. After washing, each well was incubated with anti-p65 or anti-p52 antibodies for 30 min at 37° C. Wells were washed, followed by incubation with a secondary antibody conjugated to HRP. TMB (3,3',5,5'-tetramethylbenzidine) was added for 10 min. Binding was measured in a microplate reader at 655 nm.

Caspase Assay

Colorimetric assay was used to measure the activity of caspase-3 or caspase-6. In the assay, MESC2.10 neurons were pre-incubated with caspase-3 inhibitor (Ac-DEVD-CHO), caspase-6 inhibitor (Ac-VEID-CHO) or sodium salicylate (5 mg/ml) 1 hour prior to etoposide treatment, which was for an additional 6 hrs. Cells were lysed as instructed. Fifty μg of each lysate was incubated with either caspase-3 substrate (DEVD conjugated to p-nitroanaline) or caspase-6 substrate (VEID conjugated to p-nitronalaine) in a 96 well plate at 37° C. for 1 hour. Enzyme activities for caspase-3 or caspase-6 were measured with a microplate reader at 405 nm. Results are shown as relative enzyme activity and represent average of three experiments.

BrdU Incorporation

To determine cell cycle activation in MESC-II, Day 6 differentiated neurons to coverslips were treated with 10 μM etoposide for 4 hours. BrdU (1 mM) was added and incubated for additional 2 hours. Cells were fixed in 5% paraformaldehyde followed by permeabilization in 70% methanol in PBS at −20° C. overnight. To denature chromatin, coverslips were immersed in 2 N HCl for 30 minutes at 37° C. and neutralized in 0.1 M borate buffer (pH 8.5) by washing 2 times for 5 minutes. To detect BrdU incorporation, coverslips were incubated with Rat-anti-BrdU (1:200). Anti-Tuj-1 (1:1000) was used to stain neurons. Goat anti rat conjugated to rhodamine and goat anti-mouse conjugated to FITC (1:500) were used as secondary. Pictures were captured with a confocal microscope.

Example 1

Induction of DNA Damage has Opposite Effects on IKKα and IKKβ in Neurons

This example illustrates that DNA damage activates IKKβ, but inhibits IKKα activity.

Figure 1:
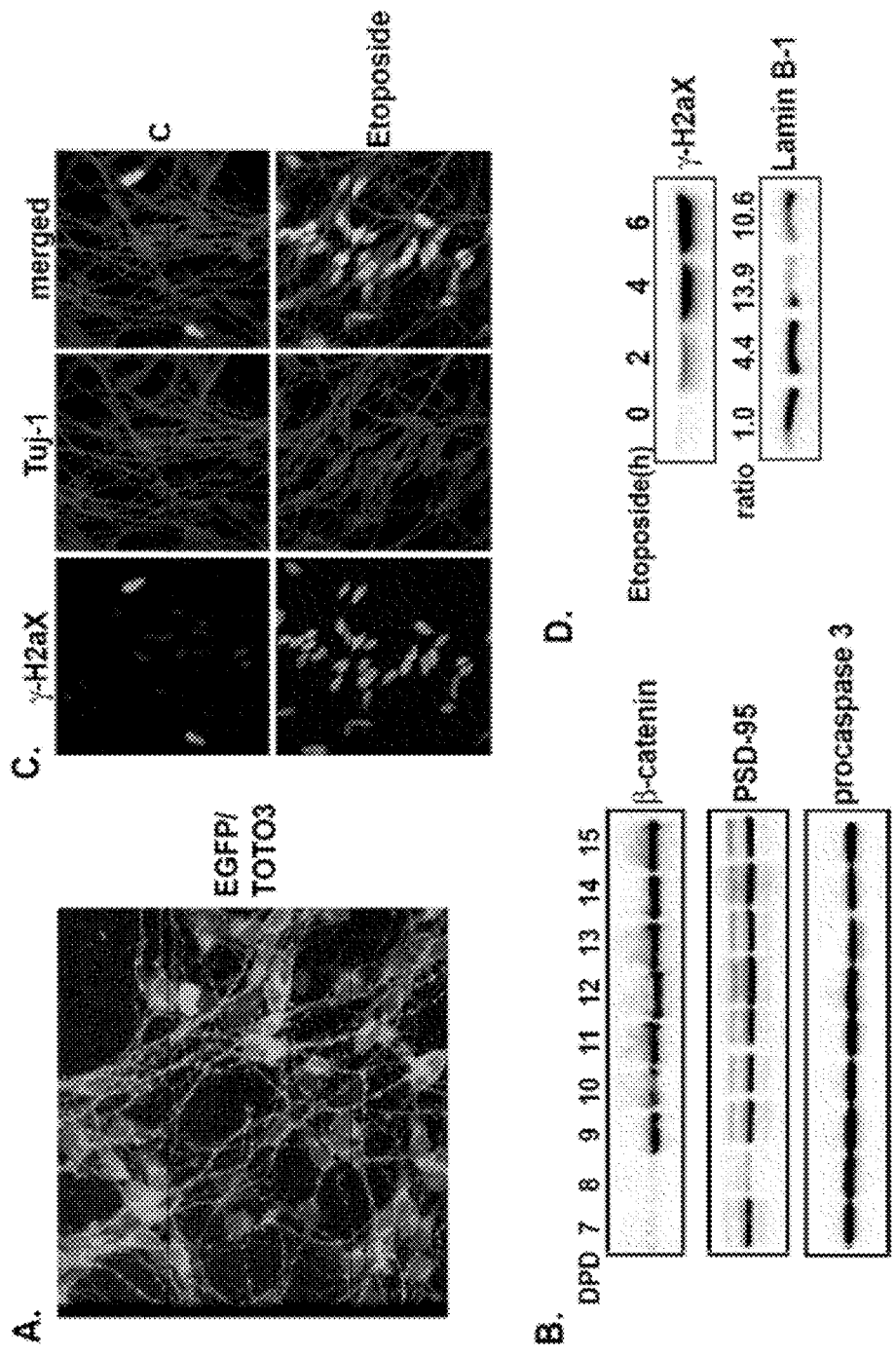
FIGS. 1A-1D show etoposide induces DNA damage in MESC2.10 neurons.

A MESC2.10 human embryonic neuronal stem cell line was used to characterize the signaling between DNA damage, IKKβ activation and Htt turnover. To establish the model, MESC2.10 neuroblasts were differentiated and examined for expression of neuronal markers. Upon differentiation, MESC2.10 cells acquire neuronal morphology (FIG. 1A) and express neuron-specific proteins such as PSD-95, β-catenin and the neurofilament Tuj-1 (FIG. 1B, top two panels and 1C). These neurons can be maintained for more than two weeks without significant apoptosis (FIG. 1B, third panel). Topoisomerase inhibitor etoposide, which produces DNA double-stranded breaks in post-mitotic neurons, was used to induce DNA damage. The induction of DNA damage in MESC2.10 neurons was confirmed by nuclear staining of phosphorylated histone H2aX (γ-H2aX), a surrogate marker of DNA damage (FIGS. 1C and 1D). An acute etoposide treatment of 6 hour was used to avoid neuronal death, which occurs after prolonged incubation.

1. DNA Damage Activates IKK in Neurons.

Figure 2:
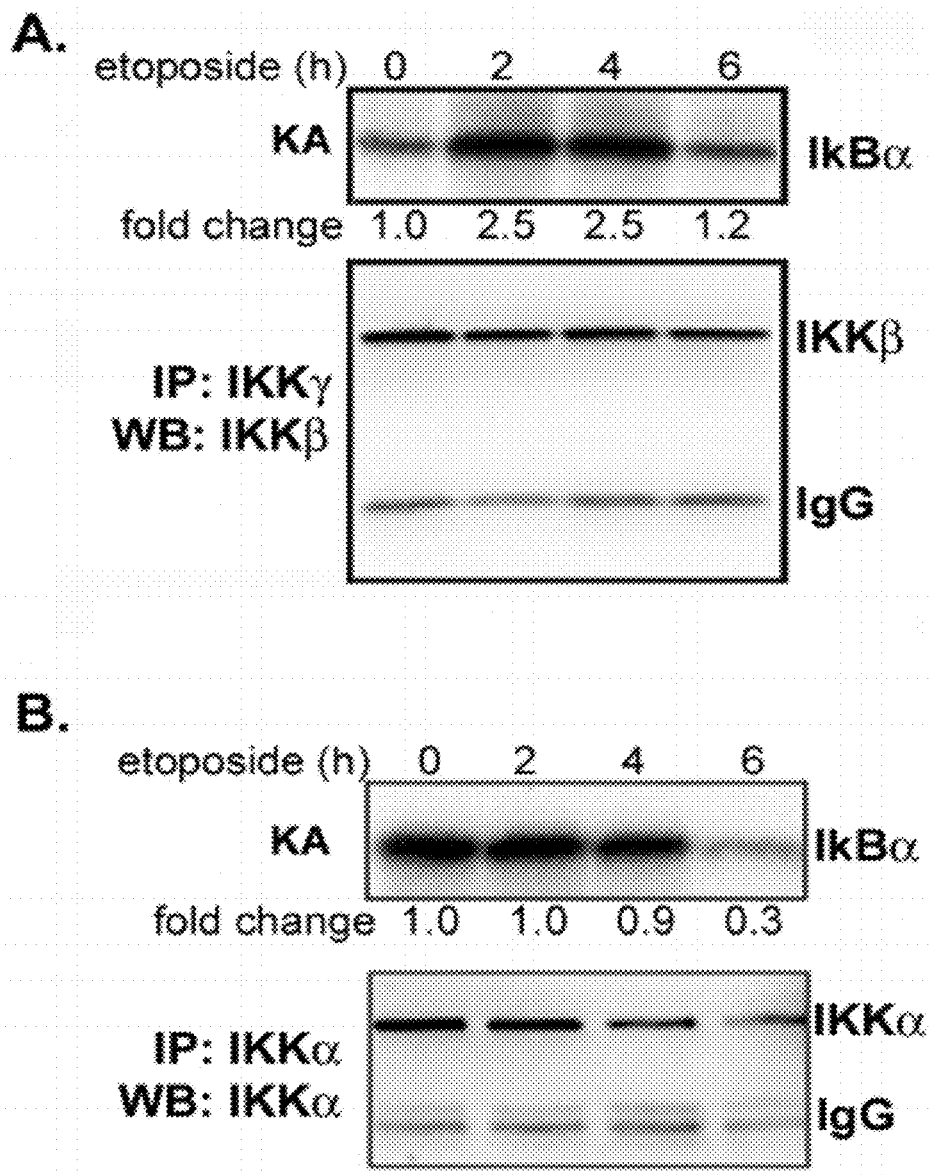
FIGS. 2A-2B show etoposide promotes IKKβ and inhibits IKKα.

To determine if DNA damage activates IKK in neurons, in vitro kinase assays was performed using recombinant IκBα as the substrate for IKKβ complexes immunoprecipitated from the extracts of etoposide-treated neurons. IKKβ was activated 2 hours after etoposide treatment and remained active for up to 4 hours (FIG. 2A top panel). These results are consistent with the effects of etoposide on IKKβ in non-neuronal cells (Wu et al., Science, 2006, 311:1141-1146).

2. DNA Damage Reduces IKKα Activity.

To determine whether DNA damage influences IKKα activity, IKKα complexes devoid of IKKβ was obtained. Neuronal extracts were depleted by prior incubation with anti-IKKγ and anti-IKKβ antibodies, and IKKα complexes were subsequently immunoprecipitated. MESC2.10 neurons display constitutive IKKα activity (FIG. 2B, top lane 1). Longer treatment with etoposide, however, reduces IKKα activity (FIG. 2B, lanes 4). A decrease in the level of IKKα protein was also observed, which may have contributed to the low IKKα activity (FIG. 2B, bottom panel).

Example 2

DNA Damage-Induced Proteolysis of Htt is Regulated by IKKs

This example illustrates that DNA damage induces proteolysis of endogenous wildtype and mutant Htt, and that IKKs regulate DNA-damage-induced proteolysis of Htt.

Figure 3:
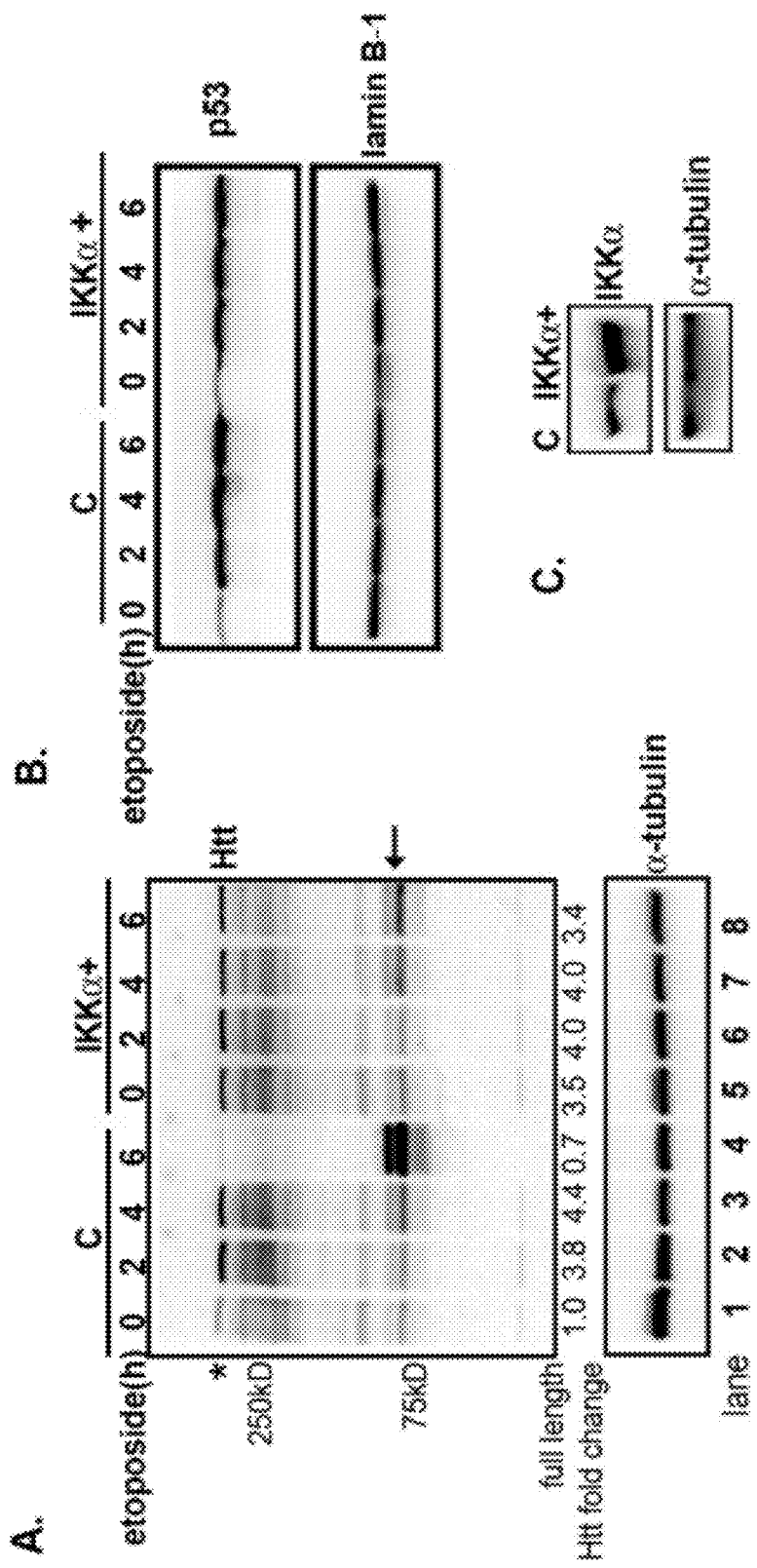
FIGS. 3A-3D show that etoposide promotes Htt proteolysis and the elevated IKKα expression inhibits Htt proteolysis.
Figure 3:
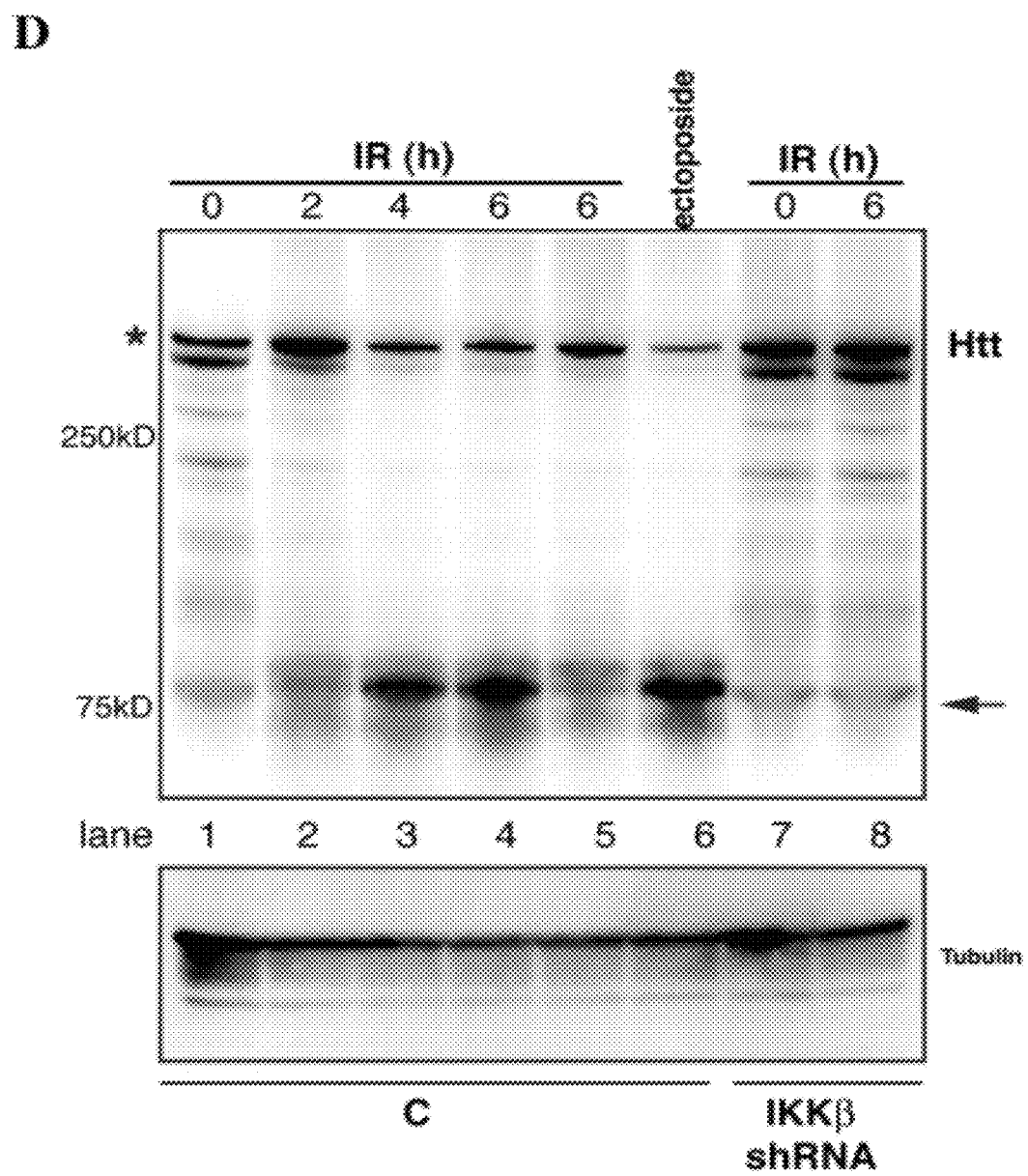

The treatment of MESC2.10 neurons with etoposide increased the level of endogenous, full-length Htt ~4-fold (FIG. 3A, top panel, asterisk, lanes 1-3). The elevation of Htt overlaps in time with accumulation of nuclear p53 (FIG. 3B, top panel, lanes 1-4). Longer exposure of neurons to etoposide induces proteolysis of endogenous Htt, however, generating N-terminal fragments of ~80 kDa (FIG. 3A, top panel, lane 4, arrow). These data suggest that accumulation of DNA damage in neurons activates proteolytic enzymes that can cleave Htt.

To confirm that Htt cleavage is induced by DNA damage and not other, secondary effects of etopoisde, we examined whether DNA damage induced by γ-irradiation of neurons could have a similar effect on Htt cleavage. As expected, γ-irradiation also generates an Htt fragment similar in size to that produced by etoposide treatment (FIG. 3D). Interestingly, induction of Htt proteolysis by γ-irradiation occurs faster than etoposide treatment and is prominent by 4 hr post-irradiation, whereas maximal Htt proteolysis induced by etoposide requires ~6 hr. The difference may be due to rapid induction of double stranded DNA breaks by irradiation.

Etoposide treatment reduced the level and activity of IKKα (FIG. 2B). In order to examine whether increasing the level of etoposide could rescue the effects of DNA damage on Htt protein, MESC2.10 neurons were transduced with an IKKα lentivirus, which increases the level of IKKα by ~3-fold (FIG. 3C). The transduction of IKKα lentivirus enabled the IKKα$^+$ neurons to resist etoposide-induced Htt proteolysis (FIG. 3A, top panel, lanes 5-8). IKKα$^+$ neurons displayed a higher basal level of full-length WT Htt than controls (FIG. 3A, compare lanes 1 and 5), and accumulation of p53 in IKKα$^+$ neurons (FIG. 3B, top panel, lanes 5-8) had no additional effect on Htt levels (e.g., further Htt activation). These findings support a protective role for IKKα in reducing proteolysis of endogenous, WT Htt in neurons with DNA damage.

In contrast, IKKβ activity was induced by DNA damage (FIG. 2A). In order to examine whether reducing IKKβ level was protective, we silenced IKKβ expression with a specific, anti-IKKβ small hairpin RNA (shRNA) expressed from a lentivirus (FIG. 4A), and treated the neurons with etoposide. Similar to the effect of elevating IKKα, silencing IKKβ expression reduced the proteolysis of Htt (FIG. 4B). In addition, silencing of IKKβ expression or inhibition of IKKβ kinase activity by sodium salicylate also blocked Htt cleavage induced by γ-irradiation (FIG. 3D, lanes 8 and 5, respectively). Taken together, IKKβ activation by DNA damage promoted Htt cleavage, and increasing IKKα or reducing IKKβ blocked this event.

Furthermore, etoposide-induced IKKβ activated p65 NF-κB DNA binding in MESC2.10 neurons (FIGS. 4C and D). The DNA binding activity of p65 was significantly reduced in neurons with elevated IKKα (FIG. 4C). Therefore, the protective effects of IKKα in response to DNA damage may include inhibition of IKKβ activity. However, inhibitors of NF-κB did not influence Htt proteolysis, suggesting that IKKβ regulation of Htt proteolysis was NF-κB independent (see below). Etoposide had no effect on the activation of p52 NF-κB in MESC2.10 neurons (FIG. 4D).

Example 3

IKKs Influence the DNA Damage-Induced Activation of Pro-Apoptotic Caspases

This example illustrates that IKKα and IKKβ regulate DNA damage-induced Htt proteolysis through modulating activation of caspases.

To better understand the role of the IKKs in etoposide-induced Htt cleavage, the activity of the caspases were measured. Both procaspase-3 and -6 levels were reduced after 6 hrs of etoposide treatment (FIG. 5A, lane 4), which coincided with the timing of Htt proteolysis (FIG. 3A, lane 4). Consistent with the reduction of procaspases, the extracts of etoposide-treated neurons displayed elevated caspase-3 and caspase-6 activities and were blocked by specific caspase inhibitors (FIGS. 5B and 5C, columns 2 and 3, respectively). On the other hand, neurons with elevated IKKα resisted activation of procaspase-3 and procaspase-6 (FIG. 5A, compare lanes 4 and 8). Moreover, extracts of etoposide-treated IKKα+ neurons had reduced caspase-3 and caspase-6 activity (FIGS. 5B and 5C, column 6, respectively). Blocking IKKβ activity with sodium salicylate, a potent inhibitor of IKKβ, or silencing IKKβ expression by shRNA also lowered the etoposide-induced activation of caspases (FIGS. 5B and 5C, columns 4 and 8, respectively). Thus, IKKα and IKKβ have opposite effects on caspase activation in the context of DNA damage, which is consistent with their differential effects on Htt cleavage.

Example 4

DNA Damage-Induced IKKβ Regulates Bcl-xL

This example illustrates that IKKβ regulates Bcl-xL through phosphorylation.

The level of intact Bcl-xL was reduced in extracts of neurons treated with etoposide (FIG. 6A, lane 6). In contrast, etoposide treatment did not affect Bcl-xL in neurons with elevated IKKα or reduced IKKβ expression (FIG. 6A, lanes 2 and 4, respectively). To confirm that Bcl-xL was important for blocking of DNA damage-induced Htt proteolysis, the expression of Bcl-xL was increased in MESC2.10 neurons using a recombinant lentivirus (FIG. 6B, second panel, lanes 3 and 4). Elevated Bcl-xL prevents DNA damage-induced Htt proteolysis and this overlapped in time with prevention of caspase-3 activation (FIG. 6B first and third panels, respectively). Overall, these studies indicated that Bcl-xL level was a critical component of caspase-mediated Htt proteolysis induced by DNA damage, and is likely influenced by IKKβ.

The level of Bcl-xL mRNA in MESC2.10 neurons was not affected by etoposide, indicating that Bcl-xL reduction was likely due to enhanced protein turnover. Although phosphorylation-induced degradation of Bcl-xL in the presence of genotoxic agents is a necessary step for induction of apoptosis, it is unclear which kinase(s) mediates this event. The possibility that activated IKKβ phosphorylates Bcl-xL was tested. To avoid contamination with other neuronal kinases that may co-immunoprecipitate with IKKβ, recombinant IKKs were used for in vitro kinase assays with Bcl-xL as the substrate. As shown in FIG. 6C, IKKβ phosphorylates Bcl-xL (top panel). The phosphorylation was specific since inhibition of IKKβ by sodium salicylate prevented the reaction, and IKKα did not phosphorylate Bcl-xL.

Thus, IKKβ is a novel kinase that modifies Bcl-xL and reduces its level in stressed, post-mitotic neurons. The finding was consistent with the unchanged levels of Bcl-xL in etoposide-treated neurons in which IKKβ expression has been silenced (FIG. 6A).

Example 5

DNA Damage-Induced Htt Proteolysis is polyQ-Independent

This example illustrated DNA damage promotes the proteolysis of mutant Htt.

In a striatal neuronal line obtained from HD knock-in mice (Hdh$^{Q111/Q111}$), etoposide treatment also promoted cleavage of full-length, mutant Htt protein (FIG. 7, top panel, lane 2). This proteolysis was blocked by inhibition of caspase-3 or IKKβ activity (FIG. 7 top panel, lanes 3 and 4). Moreover, cleavage of Htt overlaps in time with reduction of Bcl-xL, which was prevented by inhibition of IKKβ with sodium salicylate (FIG. 7, second panel).

Taken together, these results indicate that, in post-mitotic neurons, DNA damage-activated IKKβ facilitates Htt proteolysis indirectly by promoting Bcl-xL turnover and activating a caspase pathway. Thus, in the context of neuronal DNA damage, IKKβ activation is detrimental and its inhibition is protective in HD and other neurodegenerative disorders where DNA damage plays a role.

Example 6

Activation of IKKα by IKKα Activators

This example shows that IKKα activators activate IKKα in differentiated neurons.

MESC2.10 neurons engineered to express a Flag-tagged IKKα were starved for growth factors for 8 hours. 20 ng/ml insulin-like growth factor-1 (IGF-1) and 100 ng/ml netrin were added, respectively, to the starved MESC2.10 neurons for the indicated time. Neurons were harvested and cytoplasmic extracts were used to immunoprecipitate IKKα using agarose beads coupled to anti-Flag antibody. Complexes were assayed for the ability to phosphorylate a recombinant substrate GST-IκBα in the presence of radioactive γ-32P. Products were examined by SDS-PAGE followed by autoradiography (top Panel). The bottom panel shows western blotting of the duplicated immunoprecipitated IKKα used in the kinase assay. Fold changes of IKK activity were quantified by measuring the band intensity using Image J, and compared to non-treated neurons. FIGS. 9A and 9B shows that both IGF-1 and netrin activates IKKα in differentiated neurons.

Example 7

Identification of Therapeutics for the Treatment of HD

This example illustrates the identification of compounds that can be used to treat or prevent HD.

Compounds to be tested for effective therapeutics for HD are provided. As discussed above, the compounds can be, without limitation, small molecules, nucleic acids, peptides, polypeptides, or antibodies. In some embodiments, the compounds are initially screened for their ability to inhibit IKKβ. Compounds that inhibit IKKβ are then tested for their ability to inhibit or reduce the cleavage of Htt, for example through monitoring one or more cleaved Htt products or by monitoring the cells' survival. Compounds that are able to inhibit Htt proteolysis can then tested for their ability to protect cells from toxic Htt cleaved products.

In other embodiments, compounds are provided that are related to known Htt proteolysis inhibitors, such as known IKKβ inhibitors, known caspase inhibitors, known Bcl-xL inducers. For example, the IKKβ inhibitors may be structurally related. These compounds can be tested for their ability to inhibit IKKβ activity and, if they appear to be candidate IKKβ inhibitors, are then tested for their ability to inhibit or reduce DNA-damage induced Htt proteolysis.

In still other embodiments, compounds are tested directly in assays of their ability to protect cells from the toxic Htt cleaved product(s), without first directly testing their ability to inhibit Htt proteolysis.

Compounds that show some efficacy in protecting cells from the toxic effects of cleaved Htt product(s) may then be tested for their efficacy and toxicity in animal models of HD and in clinical trials on human patients.

Example 8

Treatment of Huntington's Disease

This example illustrates the treatment of a patient suffering from or at risk of developing HD.

A patient suffering from or at risk of developing HD is identified and administered an effective amount of a composition comprising one or more Htt proteolysis inhibitors. A typical daily dose for an Htt proteolysis inhibitor can range from about 0.01 µg/kg to about 1 mg/kg of patient body weight or more per day, depending on the factors mentioned above, preferably about 10 µg/kg/day to about 100 µg/kg/day. The appropriate dosage and treatment regimen can be readily determined by one of ordinary skill in the art based on a number of factors including the nature of the Htt proteolysis inhibitor, the route of administration and the patient's disease state. HD treatment efficacy is evaluated by observing delay or slowing of disease progression, amelioration or palliation of the disease state, and/or remission.

Example 9

Treatment of a DNA Damage Induced Neurodegeneration Disorder

This example illustrates the treatment of a patient suffering from or at risk of developing a DNA damage induced neurodegeneration disorder.

A patient suffering from or at risk of developing a DNA damage induced neurodegeneration disorder that is a Htt proteolysis-related disorder is identified and administered an effective amount of a composition comprising one or more Htt proteolysis inhibitors. The appropriate dosage and treatment regimen can be readily determined by one of ordinary skill in the art based on a number of factors including the nature of the Htt proteolysis inhibitor, the route of administration and the patient's disease state. Treatment efficacy of the DNA damage-induced Htt proteolysis-related disorder is evaluated by observing delay or slowing of disease progression, amelioration or palliation of the disease state, and remission. The effectiveness can be monitored by observing any change in the level of Htt proteolysis.

Example 10

Identification of DNA Damage-Induced Htt Proteolysis-Related Disorders

This example illustrates the identification of DNA damage-induced Htt proteolysis-related disorders.

A healthy subject is tested for DNA damage-induced Htt proteolysis. A subject who is suspected of having or developing a DNA damage-induced Htt proteolysis related disorder is tested for DNA damage-induced Htt proteolysis. The test for DNA damage-induced Htt proteolysis is performed through monitoring the amount of full-length Htt and/or the amount of cleaved Htt product.

A subject who has a significantly elevated level of cleaved Htt will have or be at risk of developing a DNA damage-induced Htt proteolysis-related disorder.

Example 11

Identification of IKKα Activators

This example illustrates the identification of IKKα activators.

Compounds to be tested for the potential to be effective for activating IKKα are provided. As discussed above, the compounds may be, without limitation, small molecules, peptides, nucleic acids, or antibodies.

In some embodiments, the compounds are initially screened for their ability to interact with IKKα. The candidate IKKα activator that binds to IKKα is then administered to a neuronal cell. The neuronal cells are exposed to a DNA damaging agent, which will result in Htt proteolysis. A successful IKKα activator will be able to reduce the amount of cleaved Htt in a cell that has been exposed to the DNA damaging agent in comparison to a cell that is exposed to a control substance (that is not a IKKα activator).

In some embodiments, compounds are tested for their ability to modulate the level of IKKα gene expression, preferably increasing the level of transcription of IKKα gene. The level of transcription of IKKα gene can be determined by measuring the level of IKKα mRNA or IKKα protein. In some embodiments, the IKKα activators significantly increase the level of IKKα gene expression. In some embodiments, compounds are tested for their ability to enhance the level of IKKα protein in cells. The level of IKKα protein in cells can be determined by conventional techniques such as western blot. In some embodiments, the IKKα activators significantly increase the level of IKKα protein in cells.

Example 12

Identification of Bcl-xL Inducers

This example illustrates the identification of Bcl-xL inducer.

Compounds to be tested for the potential to be effective for activating Bcl-xL are provided. As discussed above, the compounds may be, without limitation, small molecules, peptides, nucleic acids, or antibodies.

In some embodiments, the compounds are initially screened for their ability to interact with Bcl-xL. The candidate Bcl-xL inducer that binds to Bcl-xL is then administered to a neuronal cell. The neuronal cells are exposed to a DNA damaging agent, which will result in Htt proteolysis. A successful Bcl-xL inducer will be able to reduce the amount of cleaved Htt in a cell that has been exposed to the DNA damaging agent in comparison to a cell that is exposed to a control substance (that is not a Bcl-xL inducer).

In some embodiments, compounds are tested for their ability to modulate the level of Bcl-xL gene expression, preferably increasing the level of transcription of Bcl-xL gene. The level of transcription of Bcl-xL gene can be determined by measuring the level of Bcl-xL mRNA or Bcl-xL protein. The preferred Bcl-xL inducers significantly increase the level of Bcl-xL gene expression. In some embodiments, compounds are tested for their ability to enhance the level of Bcl-xL protein in cells. The level of Bcl-xL protein in cells can be determined by conventional techniques such as western blot. The preferred Bcl-xL inducers significantly increase the level of Bcl-xL protein in cells.

Example 13

Identification of Caspase Inhibitors

This example illustrates the identification of activators of caspases, such as caspase-3 and caspase-6.

Compounds to be tested for the potential to be effective for activating caspases are provided. As discussed above, the compounds may be, without limitation, small molecules, peptides, nucleic acids, or antibodies.

The compounds are initially screened for their ability to interact with one or more caspases, such as caspase-3 and caspase-6. Compounds that interact with one or more caspases are then tested for their ability to inhibit the activity of the caspase(s), for example in a colorimetric assay.

The candidate caspase inhibitor that binds to caspase is then administered to a neuronal cell. The neuronal cells are exposed to a DNA damaging agent, which will result in Htt proteolysis. A successful caspase inhibitor will be able to reduce the amount of cleaved Htt in a cell that has been exposed to the DNA damaging agent in comparison to a cell that is exposed to a control substance (that is not a caspase inhibitor).

In some embodiments, compounds are tested for their ability to modulate the expression level of one or more caspase genes, preferably increasing the level of transcription of caspase gene(s). The level of transcription of caspase gene(s) can be determined by measuring the level of caspase mRNA or caspase protein. In some embodiments, compounds are tested for their ability to reduce the level of caspase protein in cells. The level of caspase protein in cells can be determined by conventional techniques such as western blot. The preferred caspase inhibitors significantly reduce the level of caspase protein in cells.

Example 14

Monitoring Htt Proteolysis Through Full-Length Htt and/or Cleaved Htt Product(s)

This example illustrates that detection of cleaved Htt product(s) allows monitoring Htt proteolysis.

Cells, such as MESC2.10 neurons, are treated by an HPI. Cells are harvested and lysed at various time points during HPI-treatment. Cell lysate is used to detect the level of full-length Htt and/or the level of cleaved Htt product(s) by conventional techniques, such as western blot. The decrease in the amount of full-length Htt and/or the increase in the level of cleaved Htt product(s) will indicate if the HPI inhibitors block or reduce the Htt proteolysis.

Example 15

Monitoring Htt Proteolysis Through Cell Survival

This example illustrates detection of cell survival allows monitoring Htt proteolysis.

Cells, such as MESC2.10 neurons, are treated by an HPI. During the HPI-treatment, cells can be harvested at various time points for detection of cell survival and/or cell death by conventional techniques. For example, cell death can be directly inspected using trypan blue, where trypan blue can only traverses the membrane in a dead cell, but not a viable cell.

The increase in the amount and/or ratio of viable cells and/or the decrease in the amount and/or ratio of dead cells will indicate if the HPI inhibitor blocks or reduces the Htt proteolysis, and therefore protects the cells from toxic cleaved Htt product(s).

Example 16

Inhibition of DNA Damage-Induced Htt Proteolysis by Htt Proteolysis Inhibitors This example illustrates the monitoring of DNA damage-induced Htt proteolysis.

Cells, such as MESC2.10 neurons, are pre-treated with a DNA damage-inducing agent, such as etoposide or γ-irradiation. The levels of endogenous, full-length Htt at various time points of the pre-treatment by the DNA damage agent are detected by conventional techniques, such as western blot. The decrease in the level of endogenous, full-length Htt indicates that the DNA damage-inducing agent has successfully induced DNA damage and thus Htt proteolysis in the cells. The occurrence of DNA damage can also be confirmed by detecting the activity of IKKβ and IKKα. The increase in the activity of IKKβ and/or the decrease in the activity of IKKα suggest that DNA damage has occurred and induced Htt proteolysis.

Candidate Htt proteolysis inhibitors (HPI) are then provided to the cells that are receiving the DNA damaging agent. During the candidate HPI-treatment, cells can be harvested at various time points for detection of cell survival and/or cell death by conventional techniques. For example, cell death can be directly inspected using trypan blue, where trypan blue can only traverses the membrane in a dead cell, but not a viable cell.

The increase in the amount and/or ratio of viable cells and/or the decrease in the amount and/or ratio of dead cells indicates that the HPI inhibitor blocks or reduces DNA damage-induced Htt proteolysis, and therefore protects the cells from toxic cleaved Htt product(s). In addition, the dynamics and efficiency of the HPI in reducing DNA damage-induced Htt proteolysis can be determined through the amount of full-length Htt and/or cleaved Htt product(s) as illustrated in Example 14.

Example 17

Effect of Caspase Inhibitor on Htt Proteolysis

Consistent with the effects of anti-IKKβ shRNA, pre-incubation of neurons with sodium salicylate blocks etoposide-induced Htt proteolysis. Caspase-3 inhibitor Ac-DEVD-CHO and caspase-6 inhibitor Ac-VEID-CHO were used to test the effects of specific caspase inhibitors on Htt cleavage. While pre-incubation of neurons with the caspase-3 inhibitor Ac-DEVD-CHO reduced Htt proteolysis, the caspase-6 inhibitor Ac-VEID-CHO had no significant effect on Htt proteolysis. A reason for the absence of caspase-6 inhibition on Htt proteolysis could be that the etoposide-induced caspase-6 activation is downstream of caspase-3. Moreover, since Htt protein has several caspase-3 sites and only one caspase-6 site at ~500-600 amino acid region, proteolysis by caspase-3 may dominate in a DNA damage paradigm.

Example 18

Caspase activity in neuron is regulated by the pro-survival protein Bcl-xL. The level of intact Bcl-xL was reduced in cytoplasmic extracts of neurons treated with etoposide. In contrast, etoposide treatment did not affect Bcl-xL in neurons with silenced IKKβ, or pre-treated with sodium salicylate. The level of Bcl-xL is not altered in neurons with elevated IKKα either. Thus, reduction of Bcl-xL coincides in time with Htt proteolysis, and reflects changes in IKKβ.

Since nuclear Bcl-xL is elevated in neurons with reduced IKKβ (data not shown), whether Bcl-xL could affect etoposide-induced cell cycle in MESC2.10 neurons was examined.

Etoposide promotes cell cycle activation in control MESC2.10 neurons measured by BrdU incorporation (FIG. 10 top panel). But neurons with silenced IKKβ do not show significant BrdU incorporation in the presence of etoposide (FIG. 10 second panel). Considering that nuclear Bcl-xL is associated with genomic stability, its accumulation in the nucleus of neurons with reduced IKKβ may prevent aberrant cell cycle activation and subsequent activation of enzymes that cleave Htt. Thus, inhibition of IKKβ activity in neurons with DNA damage can preserve both the cytoplasmic and nuclear functions of Bcl-xL.

Although the present application has been described in detail above, it will be understood by one of ordinary skill in the art that various modifications can be made without departing from the spirit of the invention. Accordingly, the present application is limited only by the following claims. All cited patents, patent applications and publications referred to in this application are herein incorporated by reference in their entirety.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

As will be appreciated by one of skill in the art, while the present specification may simply use one of the terms "comprise," "consists," or "consists essentially of," this is simply a shorthand way of describing all three possibilities, unless otherwise specified or unless the term is used in the claim (in which case the terms will have their normally accepted meanings under claim interpretation). Thus, as the terms are used above, they designate all three possibilities, unless explicitly noted otherwise.

What is claimed is:

1. A method of identifying a compound for protecting a cell from DNA damage-induced Htt proteolysis, comprising:
   providing one or more compounds to be tested;
   identifying which compound is an IKKβ inhibitor;
   testing the compound identified as the IKKβ inhibitor for its ability to reduce cleavage of Htt in a cell.

2. The method of claim 1, wherein the cell is a neuron.

3. The method of claim 1, wherein the Htt is wild type Htt.

4. The method of claim 1, wherein the Htt is mutant Htt.

5. The method of claim 1, wherein the ability of the compound to reduce the cleavage of Htt is tested by monitoring a cell's survival.

6. The method of claim 1, wherein the compound is selected from the group consisting of a small molecule, a nucleic acid, a peptide, and an antibody.

7. The method of claim 1, wherein identifying the IKKβ inhibitor comprises testing a compound for its ability to inhibit the ability of IKKβ to phosphorylate a substrate.

8. The method of claim 7, wherein the substrate is Bcl-xL.

9. The method of claim 7, wherein the compound is tested for its ability to inhibit IKKβ phosphorylation in an immune kinase assay.

10. The method of claim 1, wherein identifying the IKKβ inhibitor comprises testing a compound for its ability to inhibit activation of one or more caspases.

11. The method of claim 2, wherein the one or more caspases are selected from the group consisting of caspase-3 and caspase-6.

12. The method of claim 1, further comprising the step of applying a DNA damaging agent to the cell.

13. A method of identifying a compound for protecting a cell from DNA damage-induced Htt proteolysis, comprising:
   providing one or more compound to be tested;
   identifying which compound is selected from the group consisting of IKKα activator, Bcl-xL inducer, and some combination thereof;
   testing the compound identified as an IKKα activator, Bcl-xL inducer, or some combination thereof for its ability to reduce the cleavage of Htt in a cell.

14. The method of claim 13, wherein the cell is a neuron.

15. The method of claim 13, wherein the Htt is wild type Htt.

16. The method of claim 13, wherein the Htt is mutant Htt.

17. The method of claim 13, wherein the compound is selected from the group consisting of a small molecule, a nucleic acid, a peptide, and an antibody.

18. The method of claim 13, wherein the ability of the compound to reduce the cleavage of Htt is tested by monitoring a cell's survival.

19. The method of claim 13, wherein the ability of the compound to reduce the cleavage of Htt is assayed through monitoring the cleaved Htt product.

20. The method of claim 13, wherein identifying the IKKα activator comprises testing the compound for its ability to inhibit the phosphorylation of Bcl-xL.

21. The method of claim 13, wherein identifying the IKKα activator comprises testing the compound for its ability to inhibit activation of one or more caspases.

22. The method of claim 21, wherein the one or more caspases are selected from the group consisting of caspase-3 and caspase-6.

23. The method of claim 13, wherein identifying the Bcl-xL inducer comprises testing compounds for its ability to inhibit phosphorylation of Bcl-xL.

24. The method of claim 1, further comprising the step of applying a DNA damaging agent to the cell.

* * * * *